US008337385B1

(12) United States Patent
Cornell

(10) Patent No.: US 8,337,385 B1
(45) Date of Patent: Dec. 25, 2012

(54) CABINET HAVING RELAXATION CHAMBER WITH LIGHT AND SOUND

(76) Inventor: Douglas G. Cornell, Tampa, FL (US)

( * ) Notice: Subject to any disclaimer, the term of this patent is extended or adjusted under 35 U.S.C. 154(b) by 441 days.

(21) Appl. No.: 12/701,158

(22) Filed: Feb. 5, 2010

(51) Int. Cl.
*A61M 21/00* (2006.01)
(52) U.S. Cl. ............... 600/28; 600/26; 600/27
(58) Field of Classification Search .......... 600/26, 600/27, 28; 601/15, 47; 128/897, 898; 5/97, 5/113, 666, 904, 905; 362/130, 317, 351, 362/367, 405, 410, 414, 433, 453; 607/88; 313/315, 402, 407
See application file for complete search history.

(56) References Cited

U.S. PATENT DOCUMENTS

| 1,880,026 | A | * | 9/1932 | Singerman | 434/102 |
|---|---|---|---|---|---|
| 3,085,568 | A | | 4/1963 | Whitesell | |
| 3,603,195 | A | * | 9/1971 | Williams | 84/464 R |
| 3,826,250 | A | * | 7/1974 | Adams | 601/16 |
| 4,085,932 | A | * | 4/1978 | Hamano | 472/61 |
| 6,183,115 | B1 | * | 2/2001 | Durando | 362/351 |
| 6,544,165 | B1 | | 4/2003 | McNew | |
| 6,656,137 | B1 | | 12/2003 | Tyldsley et al. | |
| 6,702,767 | B1 | | 3/2004 | Douglas et al. | |
| 7,108,654 | B2 | * | 9/2006 | McNew | 600/28 |
| 7,141,028 | B2 | | 11/2006 | McNew | |
| 2007/0287881 | A1 | * | 12/2007 | Akimov et al. | 600/26 |

FOREIGN PATENT DOCUMENTS

WO   WO 2005058144 A2 *  6/2005

* cited by examiner

*Primary Examiner* — John Lacyk
*Assistant Examiner* — Eileen Foley
(74) *Attorney, Agent, or Firm* — Ronald E. Smith; Smith & Hopen, P.A.

(57) ABSTRACT

A cabinet includes a base section, a middle section, and an upper section. The base section encloses a plurality of speakers, the middle section includes a relaxation chamber for a reclining human user, and the upper section houses light fixtures that emit light at preselected frequencies related to the sound frequencies emitted by the speakers. Stationary foot and head light fixtures illuminate a foot and a head end of the relaxation chamber, respectively. A movable middle light fixture reciprocates along the length of the relaxation chamber. Each light fixture has a hexagonal housing with mirrored interior surfaces and at least one crystal through which light passes. A color disc mounted below the movable middle light fixture has translucent colored discs mounted about its periphery, only one of which is illuminated per user.

28 Claims, 34 Drawing Sheets

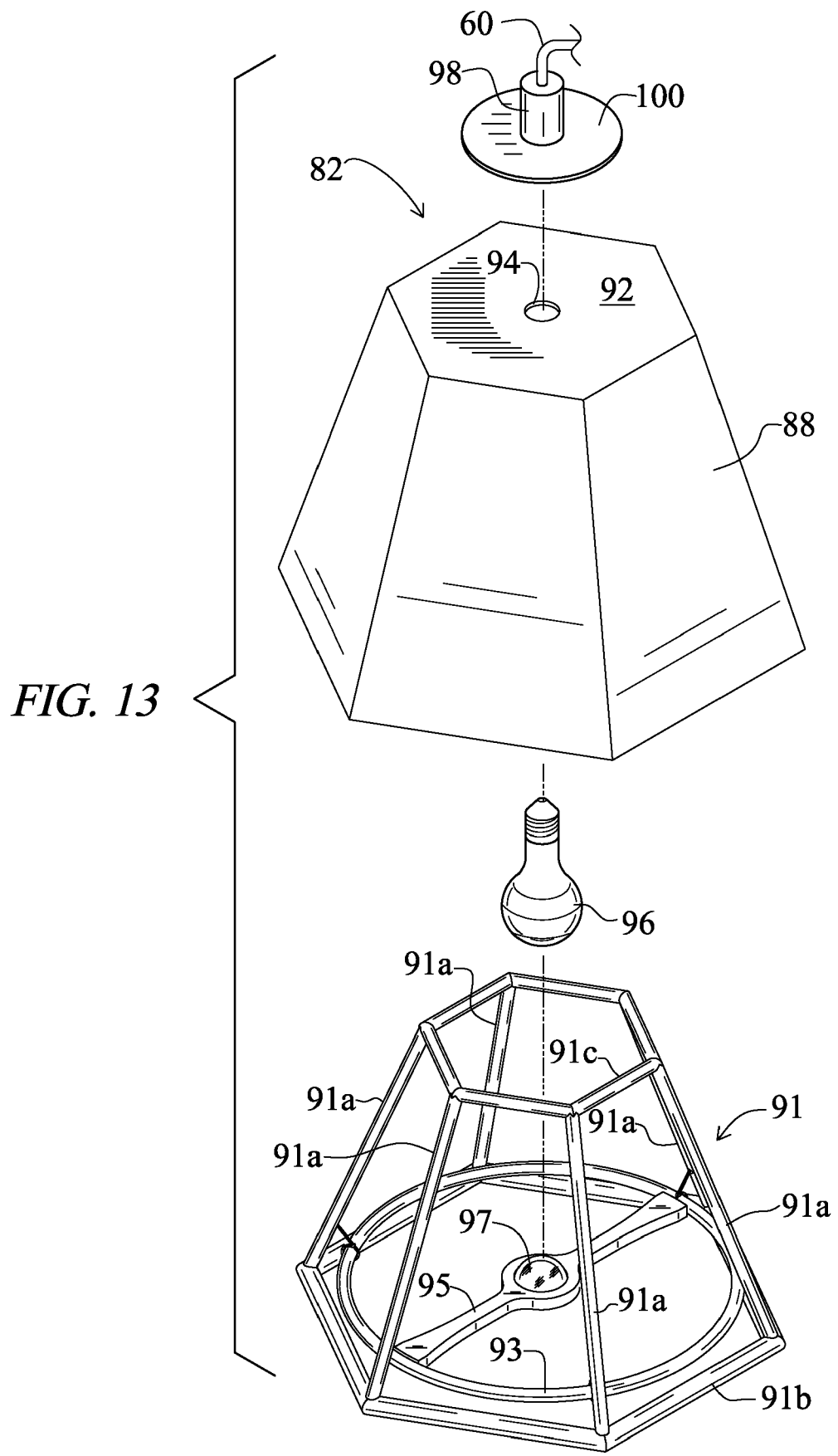

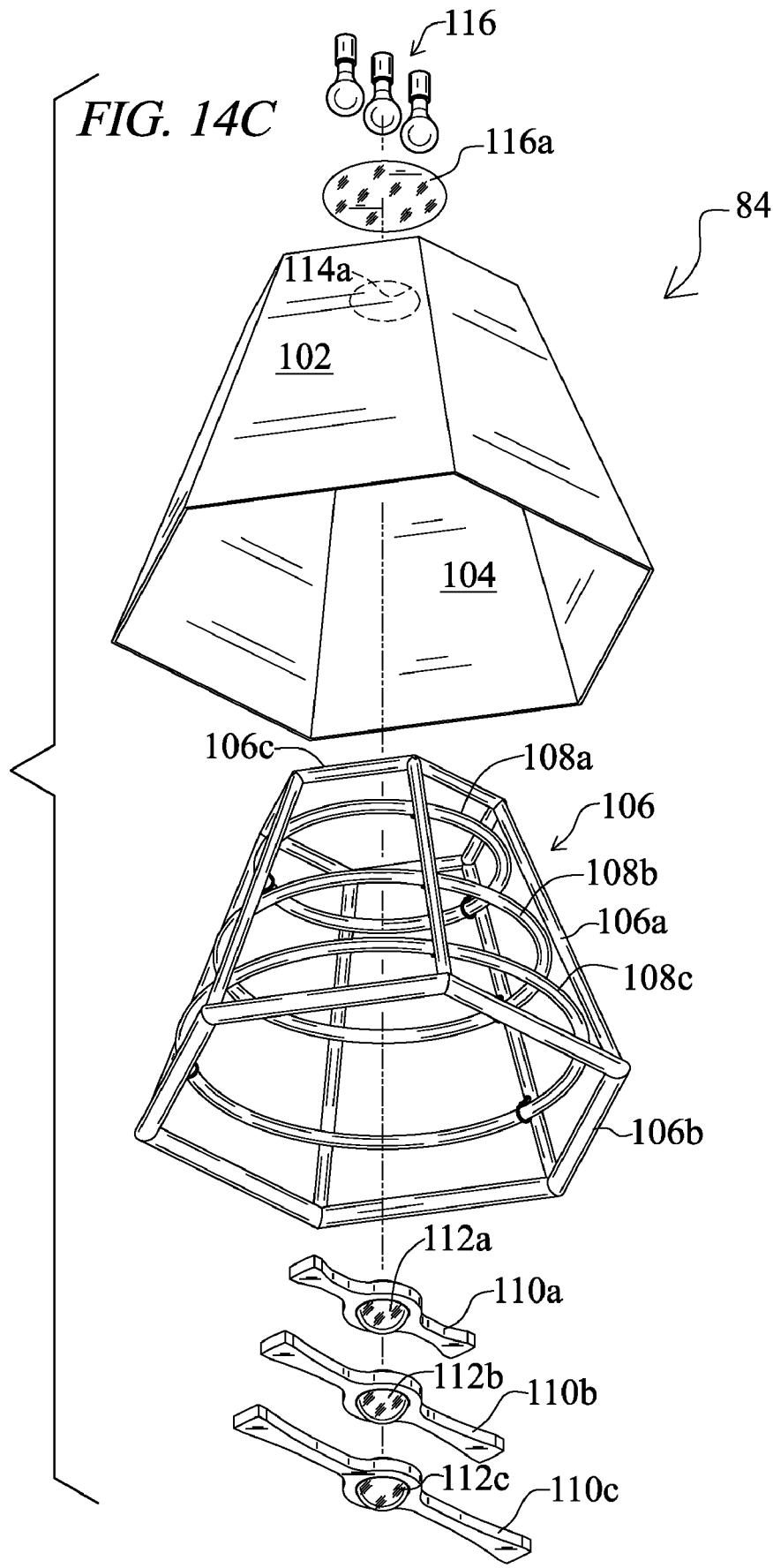

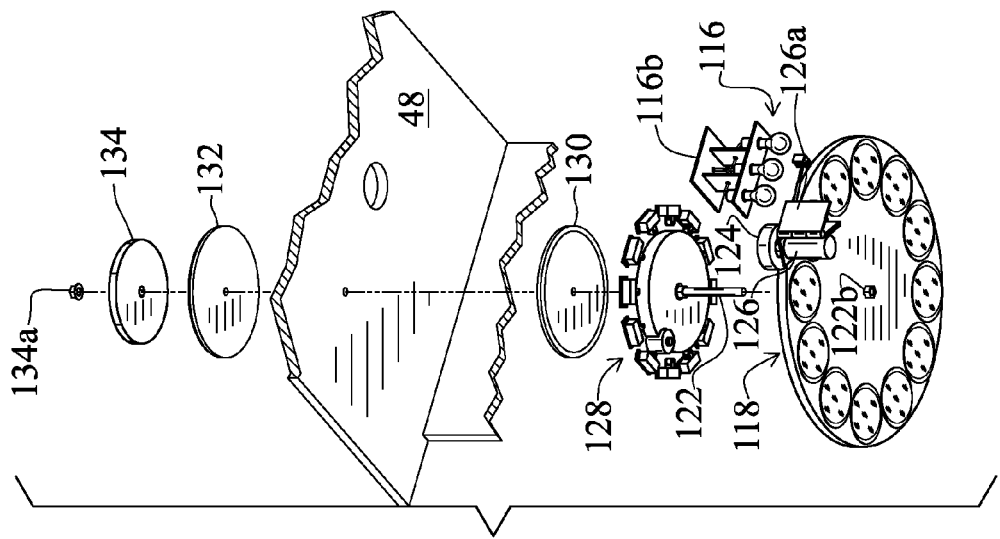
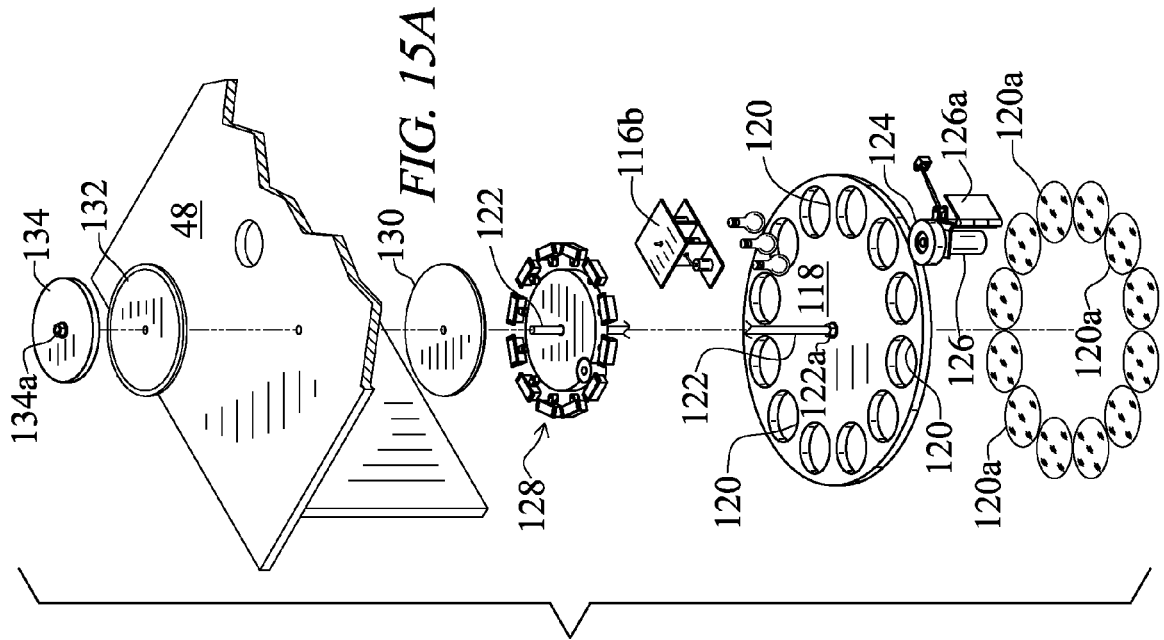

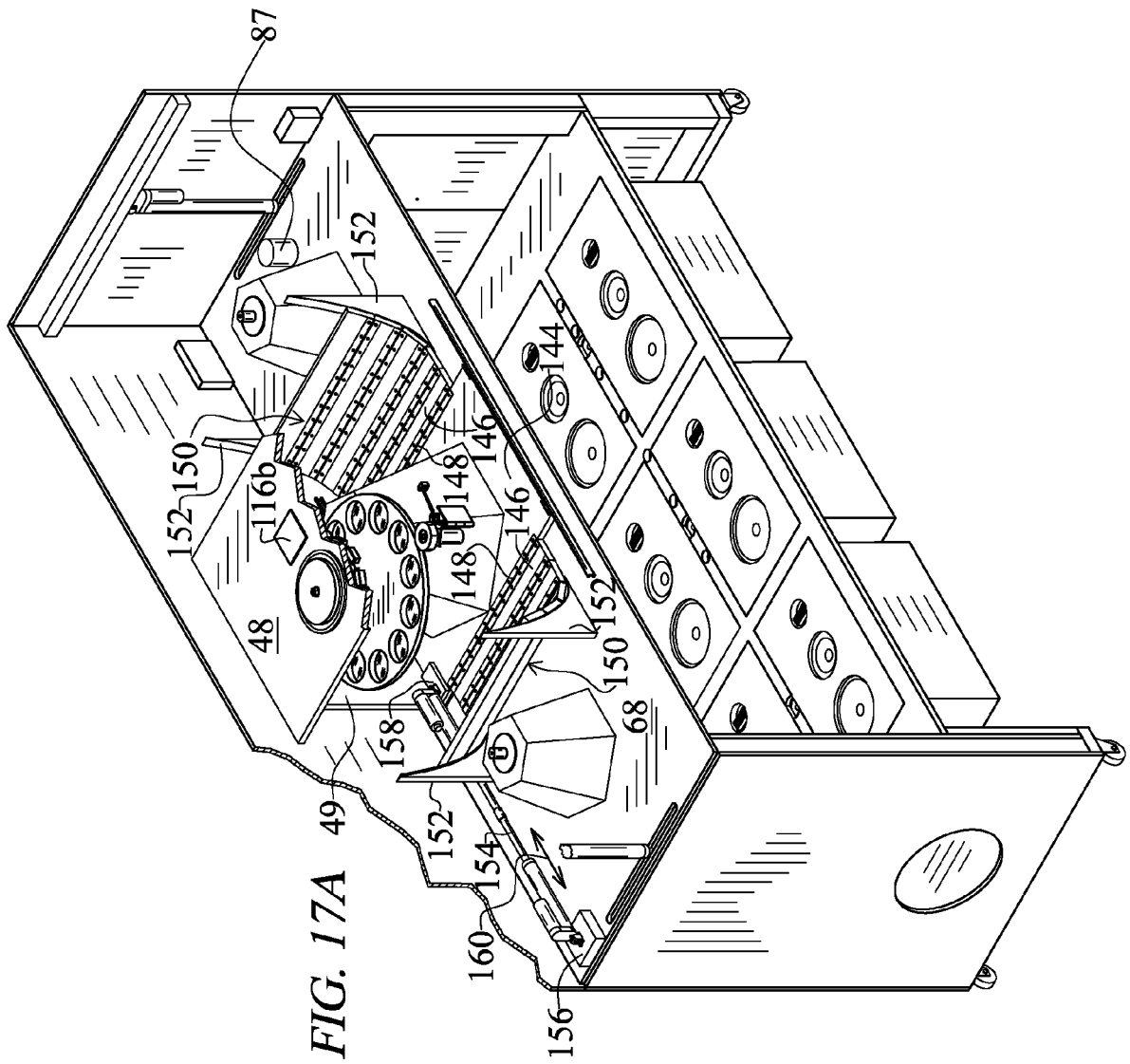

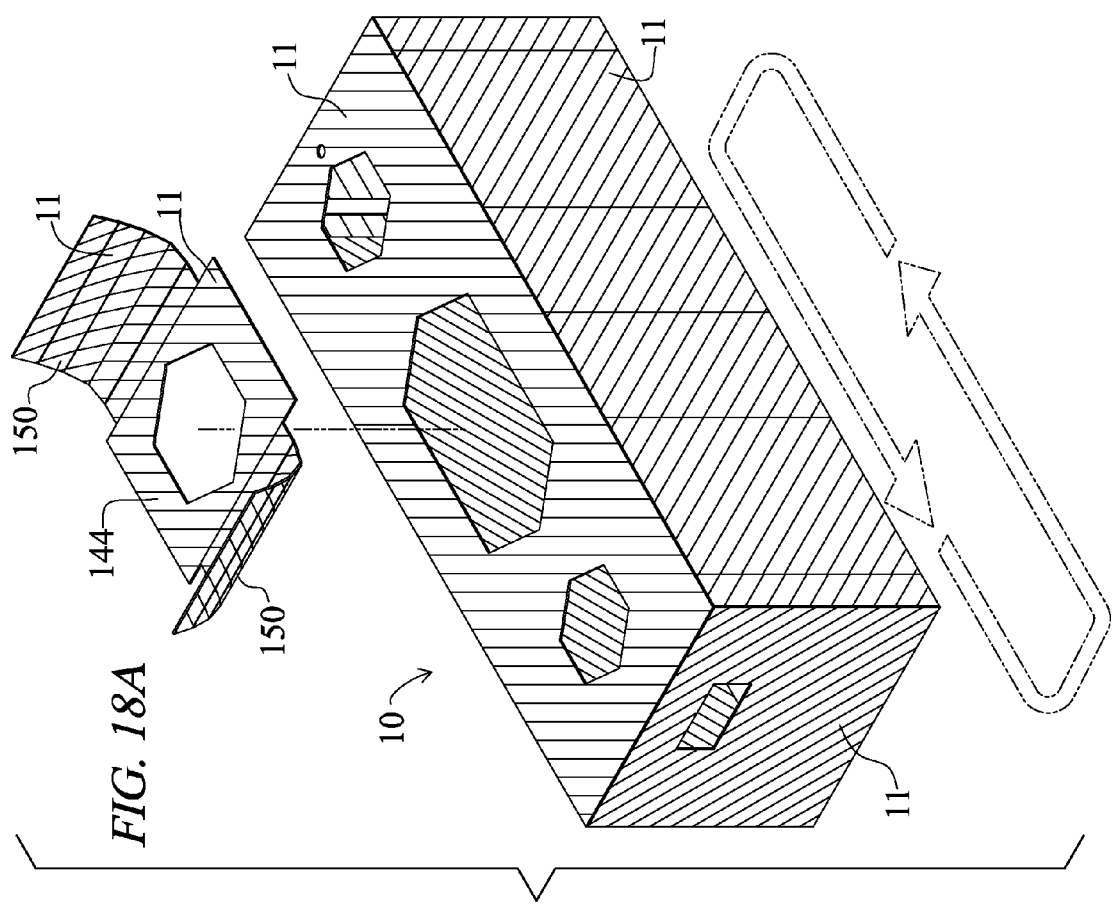

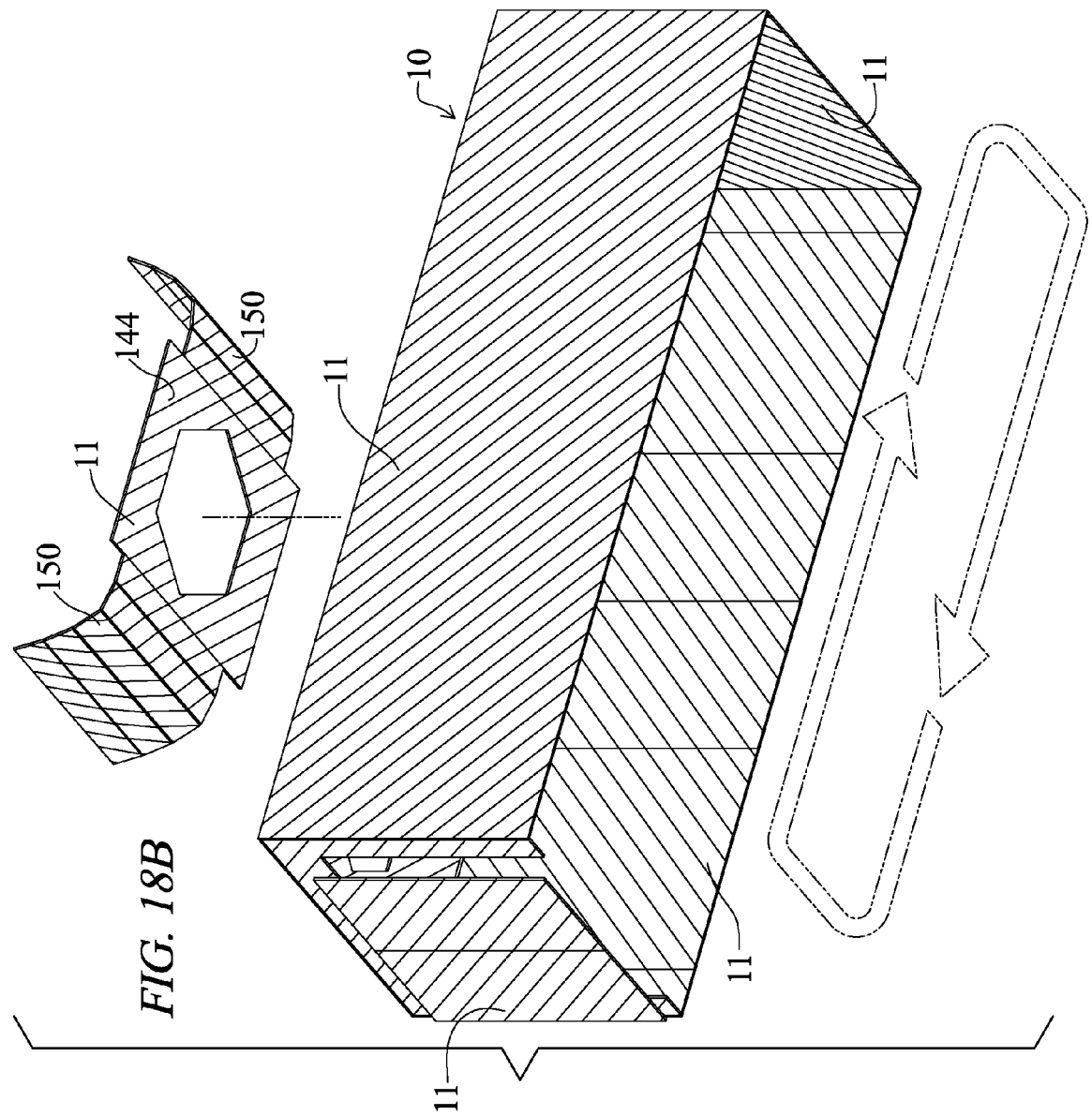

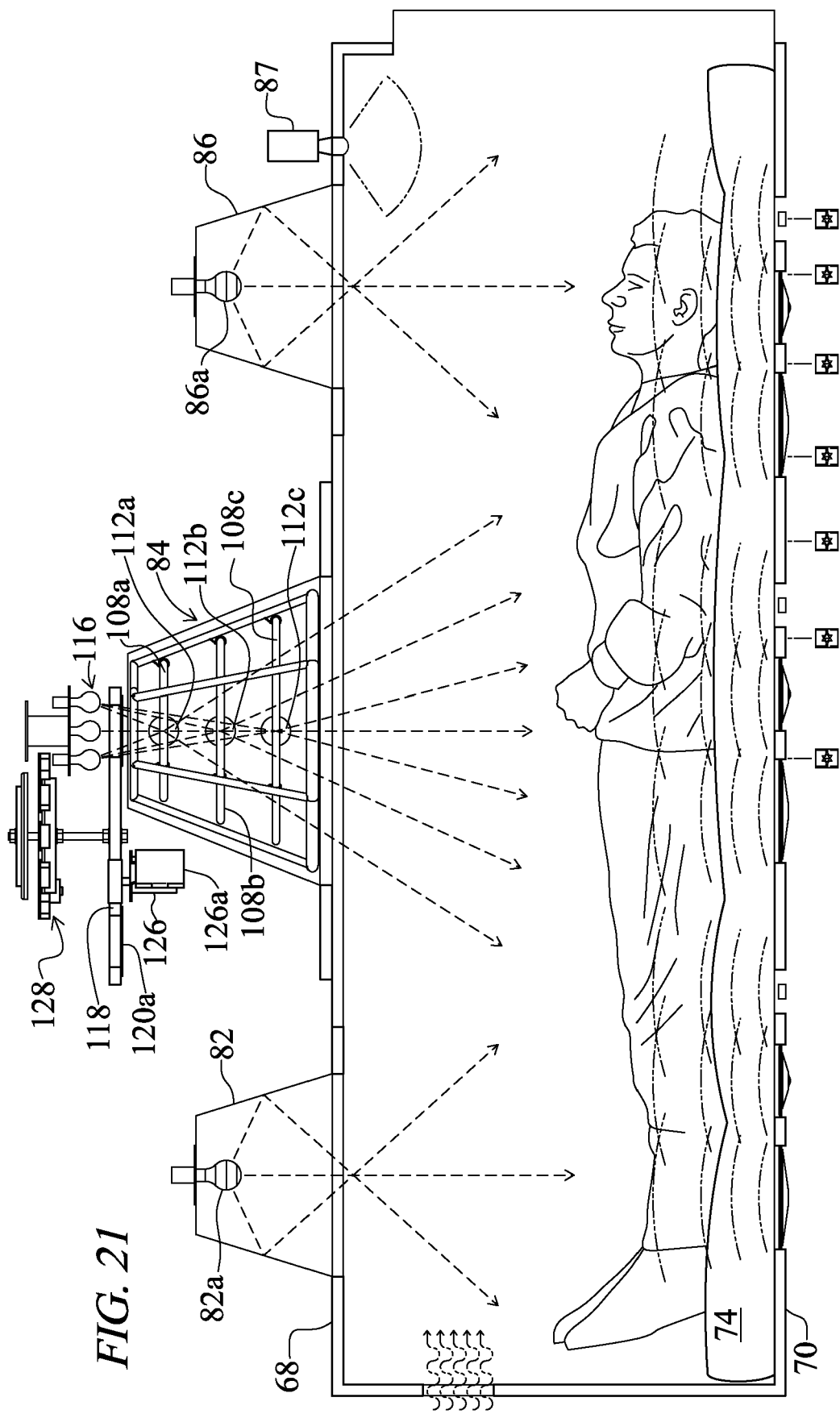

US 8,337,385 B1

CABINET HAVING RELAXATION CHAMBER WITH LIGHT AND SOUND

BACKGROUND OF THE INVENTION

1. Field of the Invention

This invention relates, generally, to relaxation devices. More particularly, it relates to a cabinet where various lights and sounds provide therapeutic benefits to a person reclining in a relaxation chamber.

2. Description of the Prior Art

Cabinets that include relaxation chambers that use lights and sounds to benefit the health or feelings of well-being to a person lying within such a chamber are well known. The known devices provide a cabinet having a relaxation chamber where a person reclines while listening to music and seeing various lights.

However, mixtures of sound and light that have no relation to one another do not provide optimal benefits. Thus there is a need for a relaxation chamber where the sounds heard by the user are related to the lights seen by the user.

In view of the prior art when considered as a whole, it was not obvious to those of ordinary skill in the art at the time the present invention was made that such a need existed and therefore it could not have been obvious how to fulfill such undetected need.

SUMMARY OF THE INVENTION

The long-standing but heretofore unfulfilled need for an improved relaxation chamber is now met by a new, useful, and non-obvious invention.

The inventive structure is a cabinet that includes a relaxation chamber. The cabinet includes a base section, a middle section, and an upper section. The base section is adapted to enclose a plurality of speakers. The middle section includes the relaxation chamber and is adapted to enclose a reclining human user of the relaxation chamber when said human user is in a reclining position. The middle section has a foot end, a middle section, and a head end corresponding to the feet, torso and head of the reclining user. The upper section houses a plurality of light fixtures.

The light fixtures of the upper section include light bulbs that emit light at preselected frequencies. The speakers of the base section emit sound in harmonic relation to the preselected light frequencies.

A stationary foot light fixture includes a light bulb disposed in the upper section in illuminating relation to the middle section of the cabinet at the foot end of the cabinet. A stationary head light fixture also includes a light bulb disposed in the upper section in illuminating relation to the middle section of the cabinet at the head end of the cabinet.

A movably mounted middle light fixture includes a light bulb disposed in the upper section of the cabinet in illuminating relation to the middle section of the cabinet.

All of the light fixtures have a hexagonal housing formed from six panels of quadrilateral shape, each of which is wider at its bottom than its top and each of which is mirrored on an interior surface thereof.

A movable housing houses the movable middle light fixture. The movable housing includes a top horizontal panel and a bottom horizontal panel that are connected to one another along their respective front and back edges by a front vertical panel and a back vertical panel. The movable middle light fixture is mounted to the movable housing for conjoint movement therewith.

A plurality of horizontal rings is mounted within the hexagonal copper frame of the movable middle light fixture in equidistantly and vertically spaced relation to one another. An uppermost ring has a diameter less than a middle ring and the middle ring has a diameter less than a lower ring.

An upper crystal holder has opposite ends secured to the upper ring and the upper crystal holder is coincident with a diameter of the upper ring. A middle crystal holder has opposite ends secured to the middle ring and the middle crystal holder is coincident with a diameter of the middle ring. A lower crystal holder has opposite ends secured to the lower ring and is coincident with a diameter of the lower ring.

A first aperture is formed mid-length of the upper crystal holder and a first crystal is secured within the first aperture. A second aperture is formed mid-length of the middle crystal holder and a second crystal is secured within the second aperture. A third aperture is formed mid-length of the lower crystal holder and a third crystal is secured within said third aperture.

Three light bulbs in linear array are disposed above the movable middle light fixture. The center bulb is centered with respect to a central aperture formed in a hexagonal plate that closes the top of the movable middle light fixture. The array of light bulbs is mounted to the movable housing so that the array moves conjointly with the movable middle light fixture when the movable housing and hence the middle light fixture are reciprocated along a longitudinal axis of the cabinet. The middle light bulb of the three bulb array remains in axial alignment with the vertical axis of symmetry of the movable middle light fixture when the movable middle light fixture reciprocates conjointly with the movable housing.

A color disc has a plurality of apertures formed therein near its periphery. A translucent colored disc is mounted within each aperture of the plurality of apertures and each translucent colored disc has a color unique to it. A drive disc is disposed in abutting relation to a peripheral edge of the color disc so that rotation of the drive disc effects rotation of the color disc about a shaft. Rotation of the color disc causes the translucent colored discs to sequentially follow a path of travel under the light bulb array. However, the color disc does not rotate after a color has been selected for a particular user of the apparatus.

An LED switch disc includes a rotatably-mounted disc-shaped central part and a stationary toroidal part that surrounds the central part in coplanar relation therewith. The LED switch disc is positioned within the movable housing in vertically spaced relation above the color disc and is concentric therewith. A plurality of LED switches, each of which includes a switch actuator, is mounted about the periphery of the toroidal part. A recess is formed in a peripheral edge of the rotatable central part of the LED switch disc and a protuberance is mounted in the recess for conjoint rotation with the rotatable central part. Each switch actuator is actuated when the protuberance abuttingly sequentially engages it as the central part of the LED switch disc rotates about a vertical shaft, there being one momentary activation of each LED switch for each revolution of the central part.

The LED switch disc is mounted in underlying relation to the top horizontal panel of the movable housing in vertically spaced relation to the color disc. The color disc is mounted above the movable middle light fixture in offset relation thereto so that as the color disc is rotated from one position to another, the translucent colored discs are sequentially brought into centered relation to a central aperture formed in a hexagonal top panel of the movable middle light fixture to align a middle light bulb of the light bulb array with the central aperture. The middle light bulb has a longitudinal axis of symmetry coincident with a longitudinal axis of symmetry of the movable middle light fixture. The color disc is rotated to align a preselected translucent colored disc with said middle light bulb prior to a client treatment but the color disc does not rotate during treatment as mentioned above.

A primary object of the invention is to advance the art of relaxation chamber cabinets by providing a relaxation chamber where a user sees lights and hears sounds that are harmoniously related to one another to enhance the benefits received by the user.

Another important object is to provide a moving light that is selected from a collection of multiple light colors according to the needs of individual users. The selected light reciprocates along the length of the relaxation chamber to provide benefits at any point or where needed along the entire length of the body of the user.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which:

FIG. 13 is an exploded top perspective view of a head or foot light fixture;

FIG. 14C is a third bottom perspective exploded view of said movable middle light fixture;

FIG. 15A is an exploded top perspective view of a color disc assembly;

FIG. 15B is an exploded bottom perspective view of said color disc assembly;

FIG. 17A is a cut-away perspective view of the novel cabinet;

FIG. 18A is an exploded top perspective view of the horizontal panel with flexible wings and the exterior of the novel relaxation chamber;

FIG. 18B is an exploded bottom perspective view of the same parts depicted in FIG. 18A;

FIG. 21 is a side elevational view depicting the relaxation chamber when occupied and with the various lights in operation.

DETAILED DESCRIPTION OF THE PREFERRED EMBODIMENT

Figure 1:
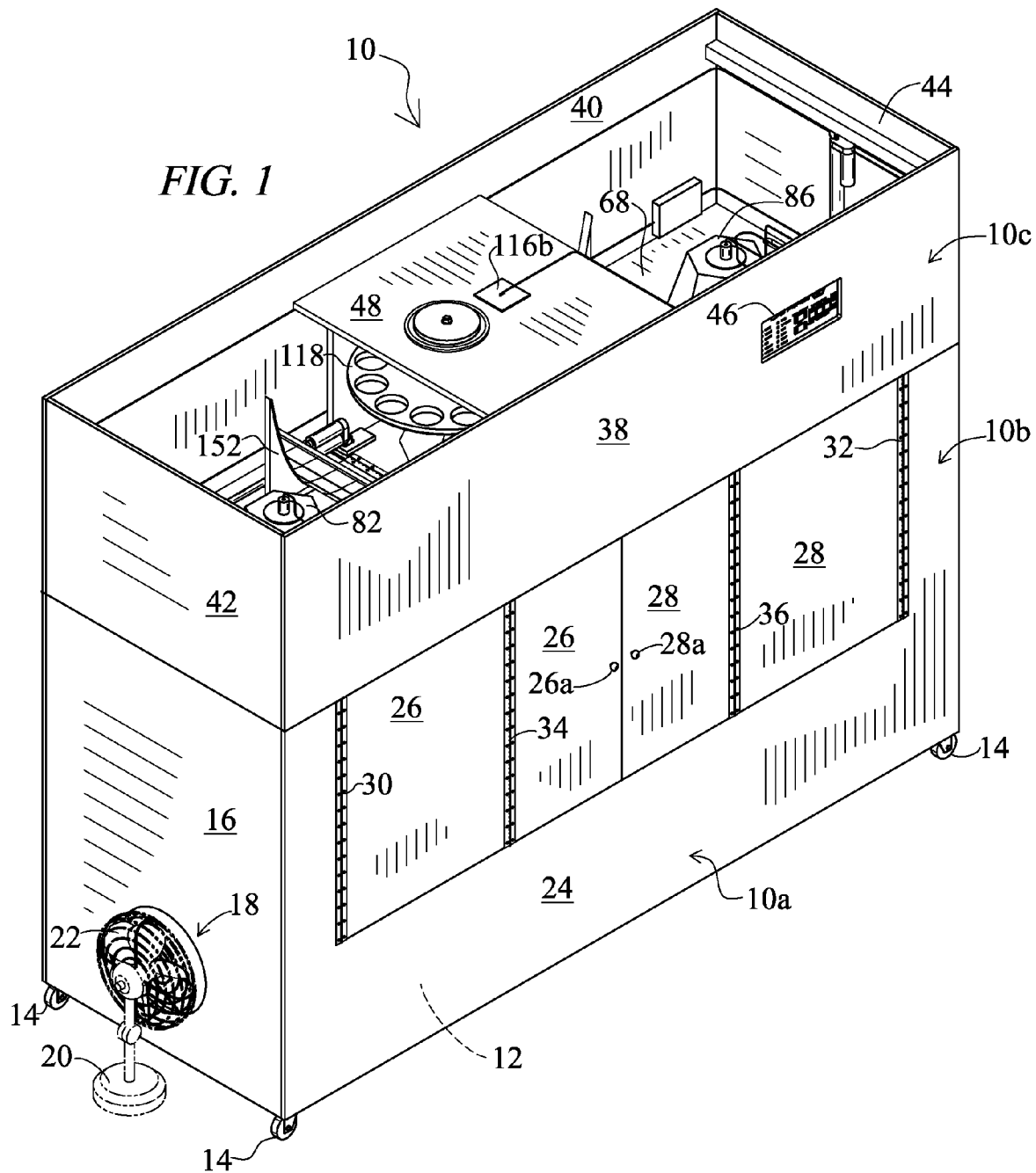
FIG. 1 is a first top perspective view of the novel cabinet.

Referring now to FIG. 1, it will there be seen that the novel apparatus is denoted as a whole by the reference numeral 10.

Cabinet 10 has a rectangular bottom wall 12 and a caster wheel 14 is mounted to said bottom wall in each of its four corners as depicted so that cabinet 10 can be moved easily from place to place.

First upstanding end wall 16, also of rectangular construction, has a circular aperture formed therein. Fan 18 includes base 20 and rotatable blades 22 protected by a cage; the cage is in registration with the circular aperture.

More particularly, cabinet 10 includes a base section 10*a*, a middle section 10*b*, and an upper section 10*c*. Fan 18 is in open communication with base section 10*a*.

Cabinet 10 further includes upstanding front wall 24 having a rectangular configuration and a rectangular opening formed therein that is closed by doors 26 and 28. Piano hinge 30 hingedly connects door 26 to said front wall and piano hinge 32 hingedly connects door 28 to said front wall. Piano hinge 34 provides a hinge about mid-length of door 26 and piano hinge 36 provides a hinge about mid-length of door 28.

Accordingly, doors 26 and 28 are bi-fold doors. Door 26 includes handle 26a and door 28 includes handle 28a. The bi-fold structure reduces the amount of clearance required to open said doors.

Middle section 10b of cabinet 10 is opened when doors 26 and 28 are open.

Top section 10c surmounts middle section 10b. Said top section houses a fixed position head light fixture, a movably mounted middle light fixture, and a fixed position foot light fixture, all of which are disclosed hereinafter. Top section 10c includes rectangular front wall 38, rectangular back wall 40, rectangular first end wall 42 and rectangular second end wall 44. Control panel 46 is mounted on front wall 38. Horizontal panel 48 is the top panel of a movable housing that reciprocates to some extent along the length of the cabinet as more fully disclosed hereinafter. The movable housing provides a mount for the movable middle light fixture and parts related to said movable middle light fixture.

Figure 2:
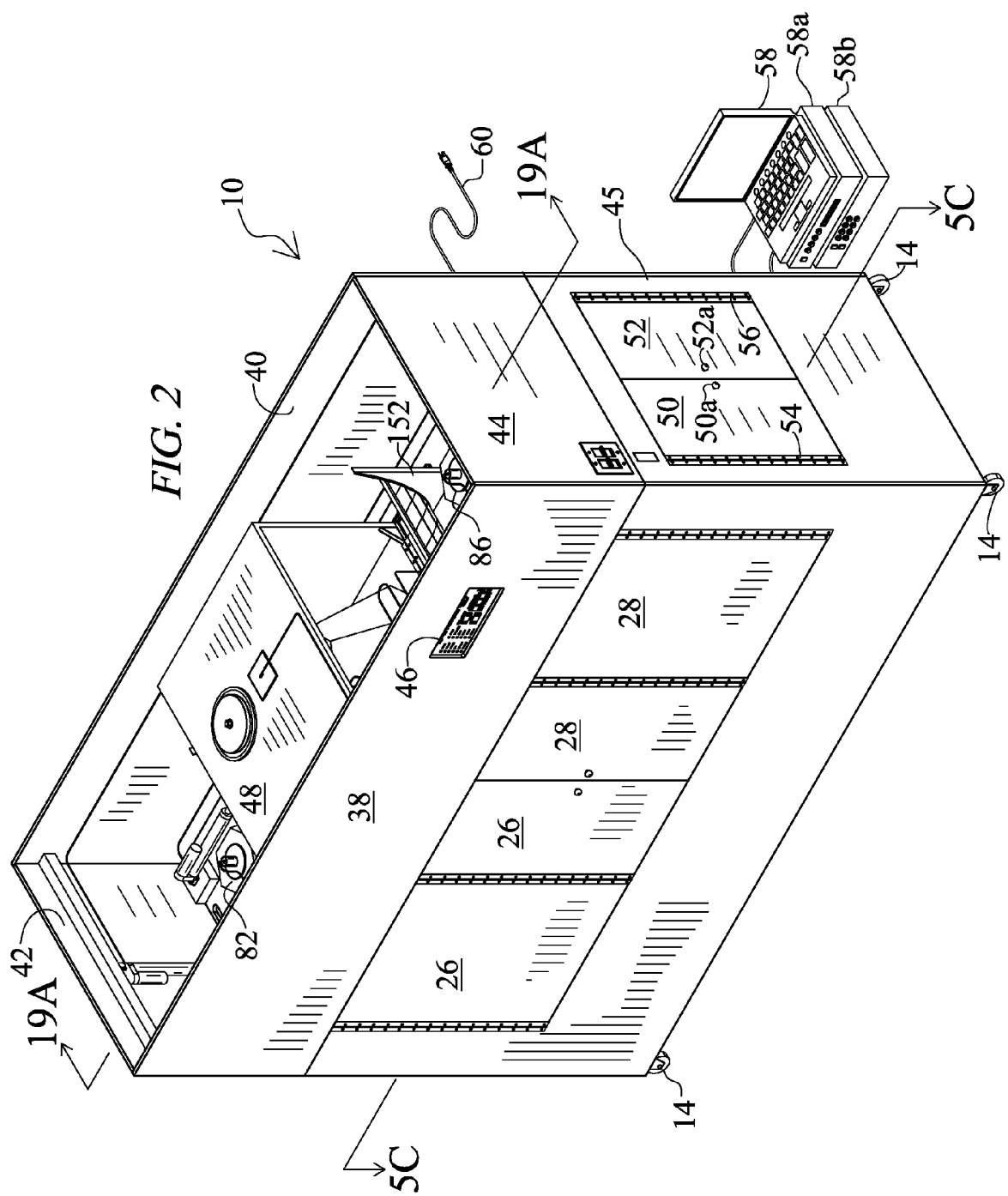
FIG. 2 is a second top perspective view of said novel cabinet.

Second end wall 44 of upper section 10c is depicted in FIG. 2. It surmounts rectangular end wall 45 of base 10a and middle section 10b. Said end wall 45 has a rectangular opening formed in it. Doors 50, 52 close said opening and are hingedly mounted by piano hinges 54, 56, respectively. Handle 50a is mounted on door 50 and handle 52a is mounted on door 52. FIG. 2 also depicts a laptop computer 58 and electrical connection 60 that provides power to the lights and speakers of the cabinet.

Figure 3:
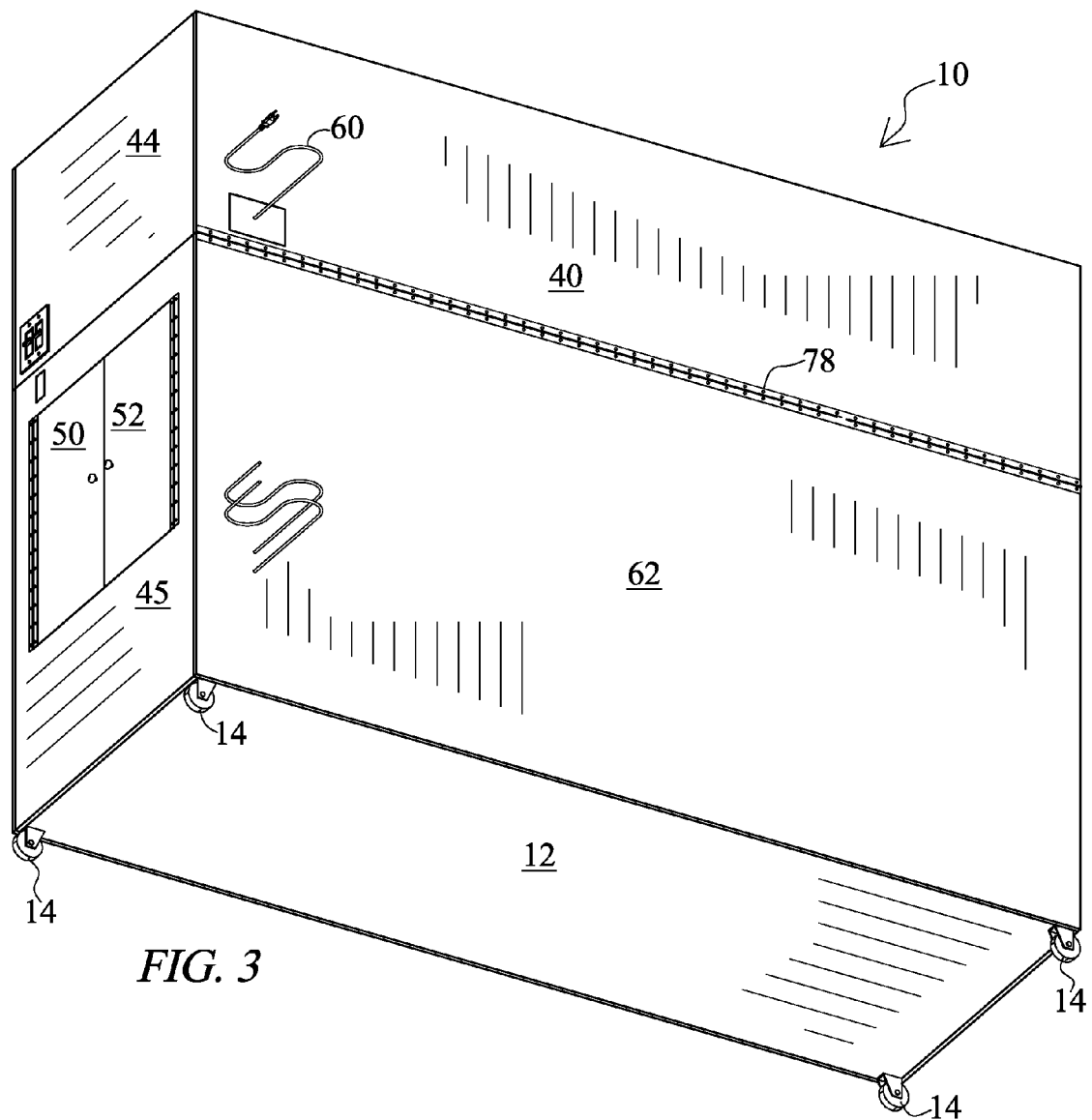
FIG. 3 is a first bottom perspective view of said novel cabinet.

Rectangular bottom wall 12 is depicted in the bottom perspective view of FIG. 3. Rectangular wall 62 is a back wall common to base section 10a and middle section 10b.

Figure 4:
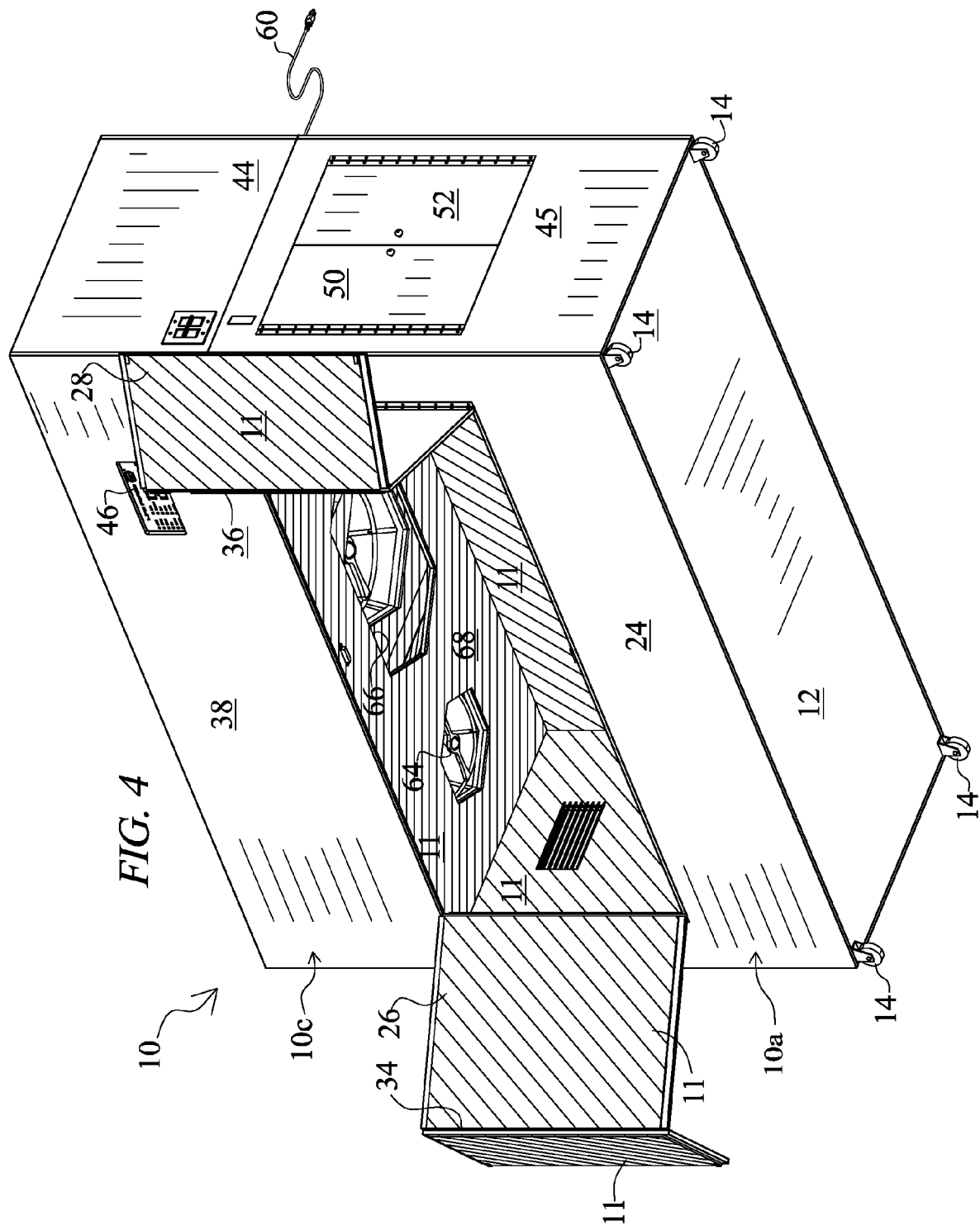
FIG. 4 is a second bottom perspective view of said novel cabinet.

The bottom perspective view of FIG. 4 depicts novel apparatus 10 with doors 26, 28 in an open configuration. The respective interior surfaces of said doors are covered with Estonian tone-wood slats 11 that are oriented at a forty-five degree (45°) angle relative to the surfaces they cover. The same wood also covers the interior side of end walls 16 and 45, back wall 62, and the bottom side of wall 68 that divides middle section 10b from top section 10c.

Openings 64 and 66 formed in top wall 68 of middle section 10b (said wall also being bottom wall 68 of upper section 10c as aforesaid) accommodate the fixed position foot light and the movable middle light, respectively. The opening that accommodates the fixed position head light cannot be seen in this view. Openings 64 and 66 are hexagonal in configuration but opening 66 is elongated in a longitudinal direction as depicted.

Figure 5A:
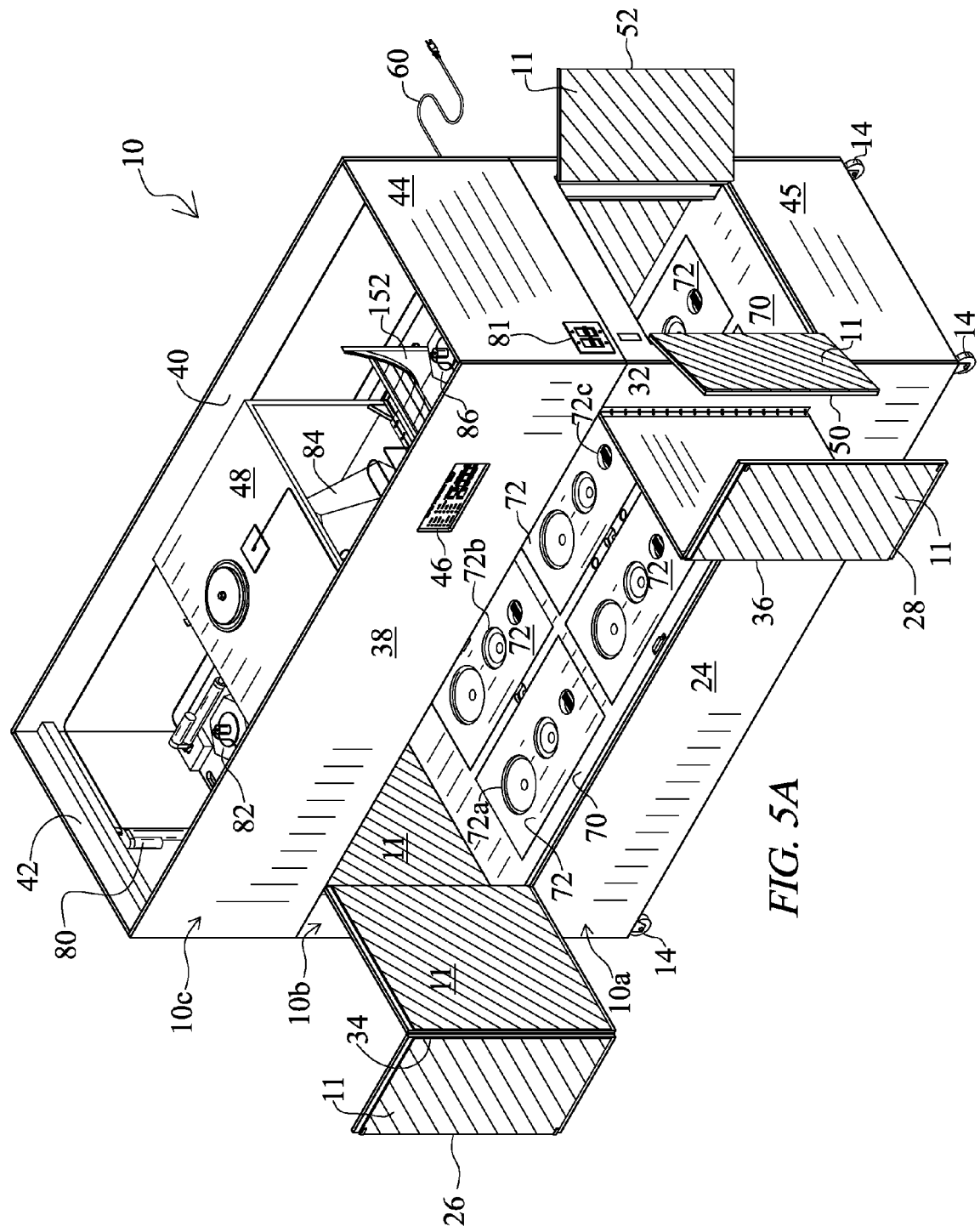
FIG. 5A is a third top perspective view of said novel cabinet.
Figure 5B:
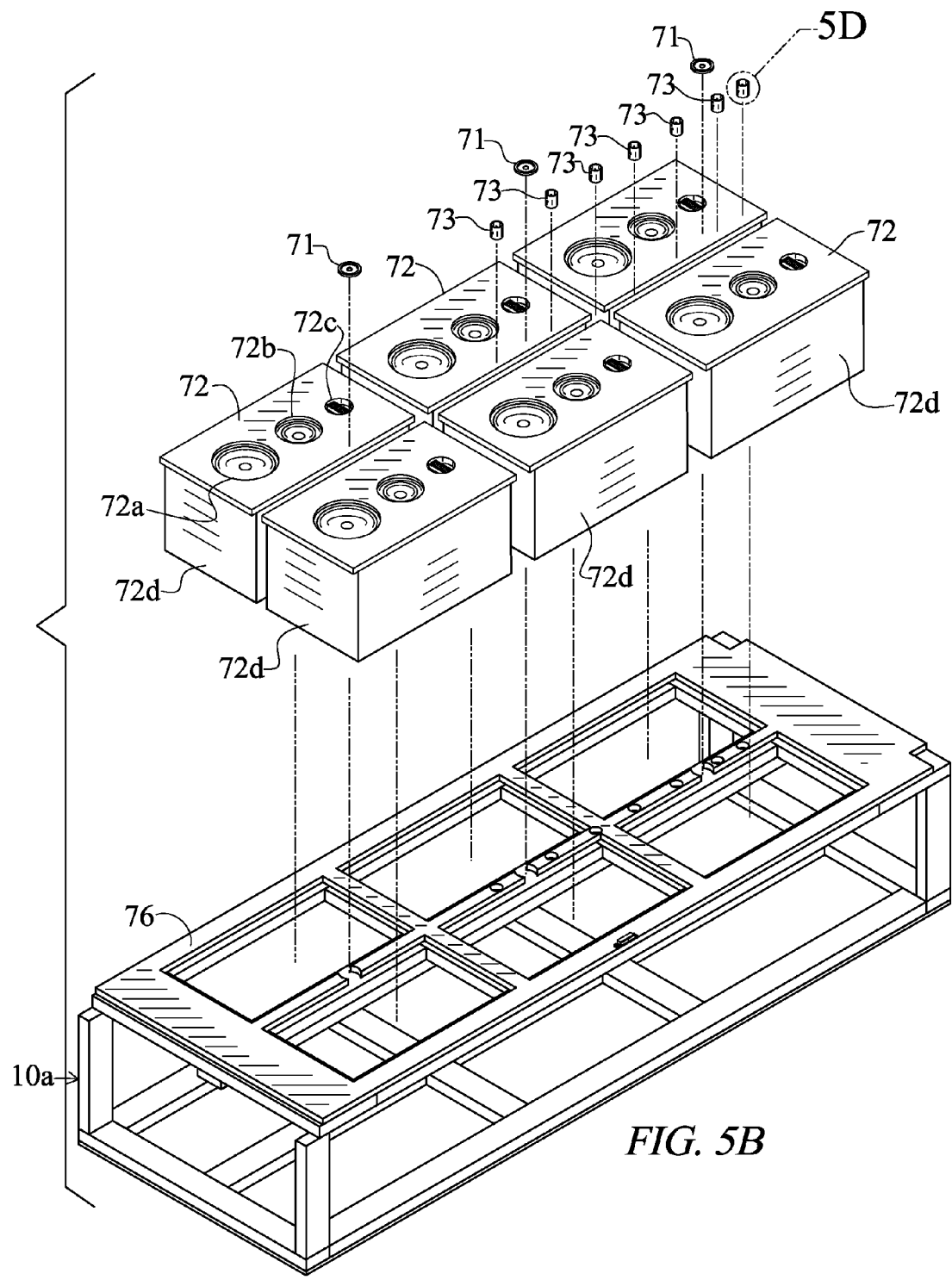
FIG. 5B is an exploded perspective view of the base section of the cabinet.
Figure 5C:
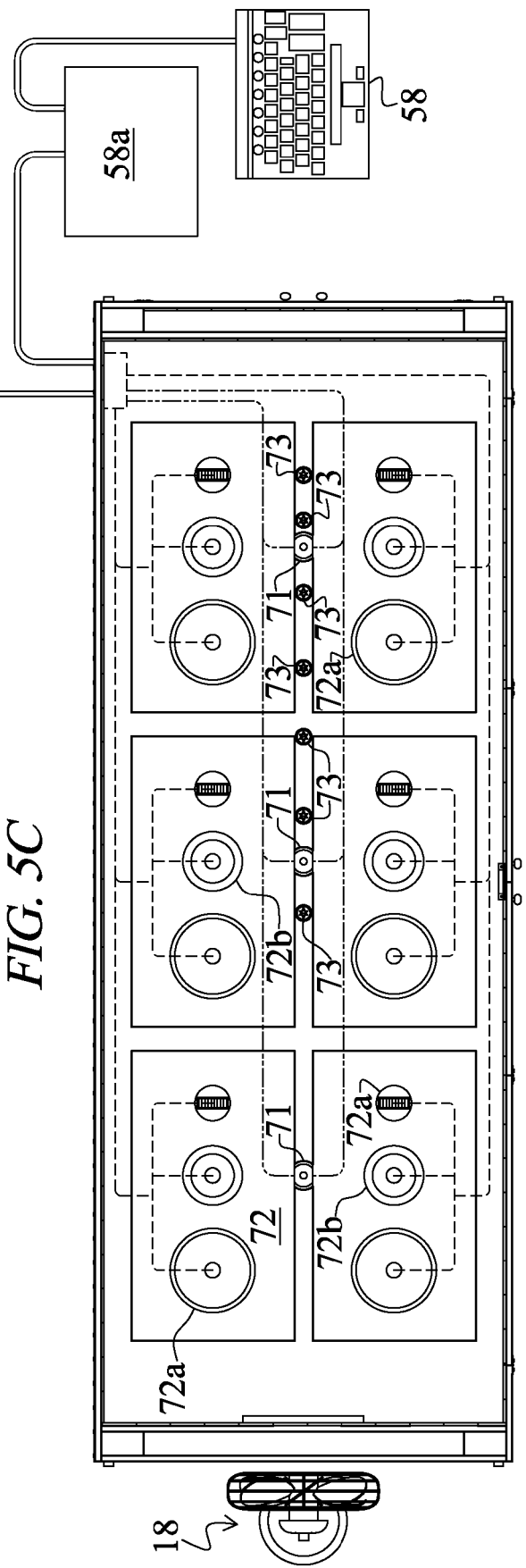
FIG. 5C is a sectional view taken along line 5C-5C in FIG. 2.

The top perspective view of FIG. 5A with doors 26, 28, 50, and 52 in their respective open configurations enables rectangular bottom wall 70 of middle section 10b to be seen. A plurality of rectangular openings is formed in said bottom wall as best understood in the exploded perspective view of FIG. 5B. Each rectangular opening is closed by a box-like enclosure 72, and each enclosure 72 has plural openings formed therein to receive speakers. The respective main bodies of the speakers are mounted in said enclosures 72 and said enclosures extend into hollow base 10a of apparatus 10. The sound-emitting end of each speaker is mounted in registration with one of said plural openings. In this particular embodiment, each box 72 accommodates a sub-woofer 72a, a mid-range speaker 72b, and a tweeter 72c. The assembly is further depicted in the top plan view of FIG. 5C.

Three (3) small Ambient® speakers, collectively denoted 71, are positioned on the longitudinal axis of symmetry of bottom wall 70 in longitudinally spaced relation to one another. They emit a constant drone frequency independent of the main music source and amplification. The circuit for speakers 72a, 72b, and 72c is separate from the circuit for speakers 71 as indicated by their separate control boxes 58a and 58b, respectively, depicted in FIG. 5C.

Control box 58a includes an amplifier and means for adjusting and regulating the sound system. Control box 58b is a frequency generator that generates frequencies that are related to the color filter in the main, central hex-light-crystal system 84. Mr. Dinshah Ghaliadi of Spectro-Chrome, Inc. calculated the equivalent sound vibration for each of twelve colors. For example, the basic frequency of the color red is 436 trillion cycles per second. To arrive at a comparable or related frequency in the audible range (reducing the frequency from visual to audible), Dinshah divided the basic color frequency by two, 40 times. That results in an audible frequency of 392 cycles per second for sound related to the color red. The corresponding sound is in the range of the ninth theoretical octave, i.e., 40 theoretical octaves below the color vibration of the visible spectrum.

Speakers 71 play the matching audible sound for each color that is selected. This enhances the effect of the selected color.

Figure 5D:
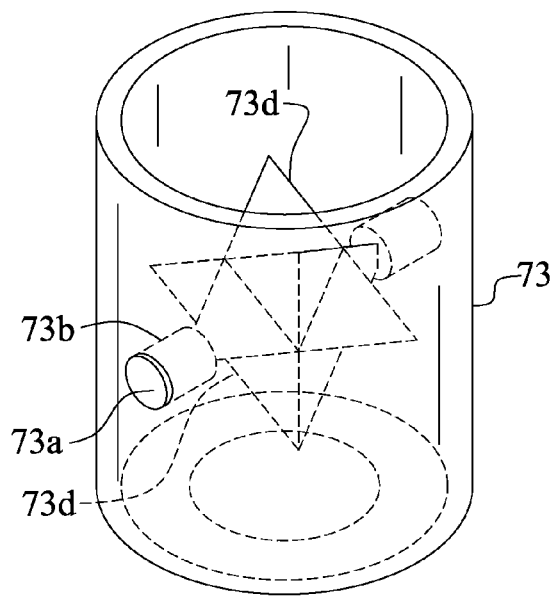
FIG. 5D is a perspective view of a copper cylindrical crystal holder.
Figure 5E:
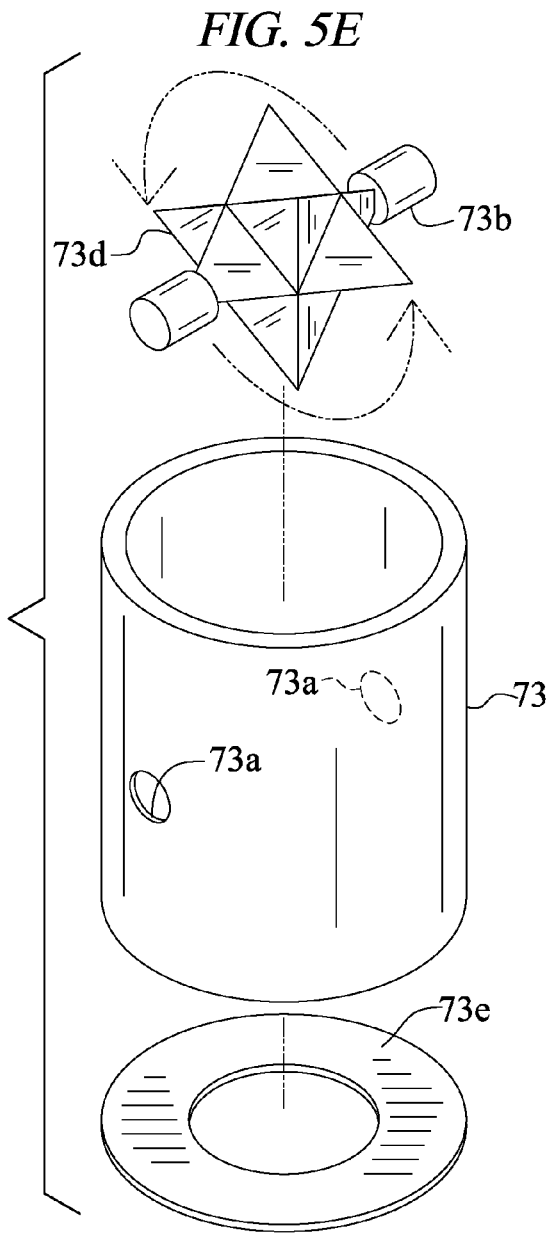
FIG. 5E is an exploded perspective view of said cylindrical crystal holder.
Figure 5F:
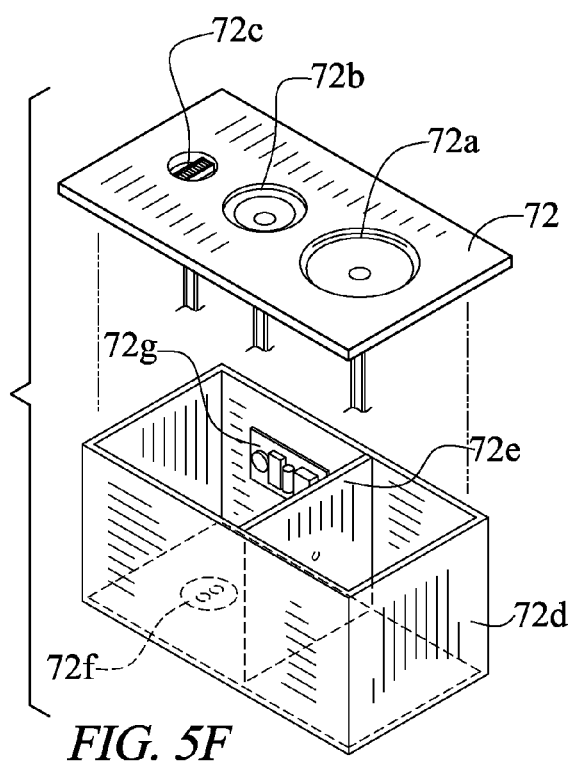
FIG. 5F is an exploded view of a speaker housing.

Items 73, also positioned on the longitudinal axis of symmetry of bottom wall 70 in longitudinally spaced relation to one another, are depicted in enhanced detail in FIGS. 5D and 5E. Each item 73 is a cylindrical housing having diametrically opposed apertures 73a formed therein for receiving opposite ends of axle 73b. Crystal 73d is rotatably mounted on each axle 73b, said rotation being indicated in FIG. 5E by the arcuate directional arrows. A merkaba crystal is the preferred crystal.

Indian yogic literature speaks of special energy centers known as "chakras" (Sanskrit) meaning "wheels," that are said to resemble whirling vortices of subtle energy. Anatomically, each major chakra is associated with a major nerve plexus and a major endocrine gland. Items 73 are aligned in the area of each of the major chakras and each crystal is a color that represents the major chakras. The crown chakra is associated with clear quartz, the third eye chakra is associated with amethyst, the throat chakra is associated with the color blue, the heart chakra is associated with the color green, the solar plexus chakra is associated with the color yellow, the sacral chakra is associated with the color orange, and the coccygeal chakra is associated with the color red. Research by Dr. Hiroshi Motoyama of Japan has presented experimental findings that confirm the presence of the chakra system in human beings.

Figure 6:
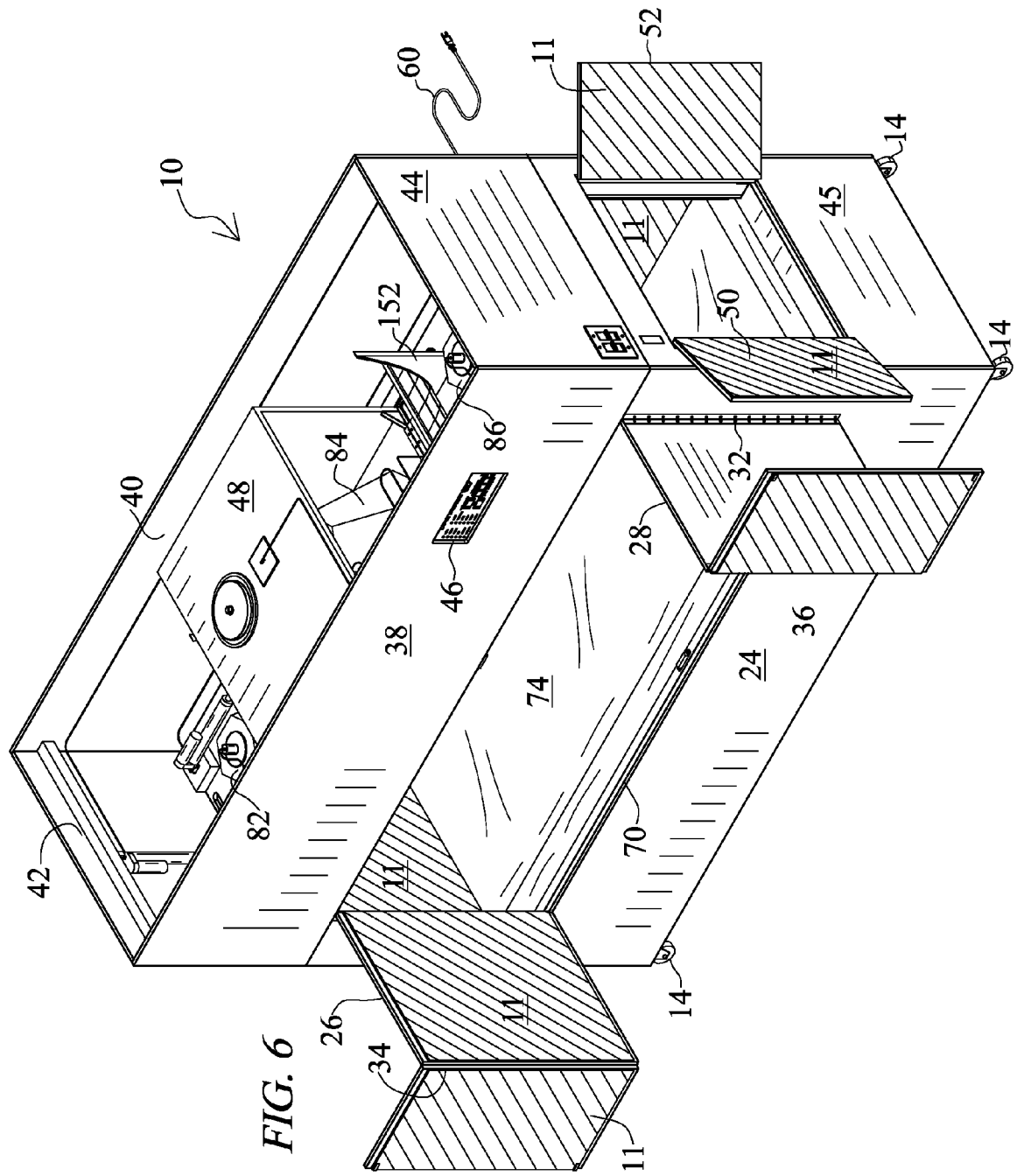
FIG. 6 is a fourth top perspective view of said novel cabinet.

Pad 74 overlies the speakers as depicted in FIG. 6. Pad 74 protects the speakers and provides a comfortable support for a user of cabinet 10 but is formed of a material that does not muffle the sound emitted by the speakers.

Figure 7:
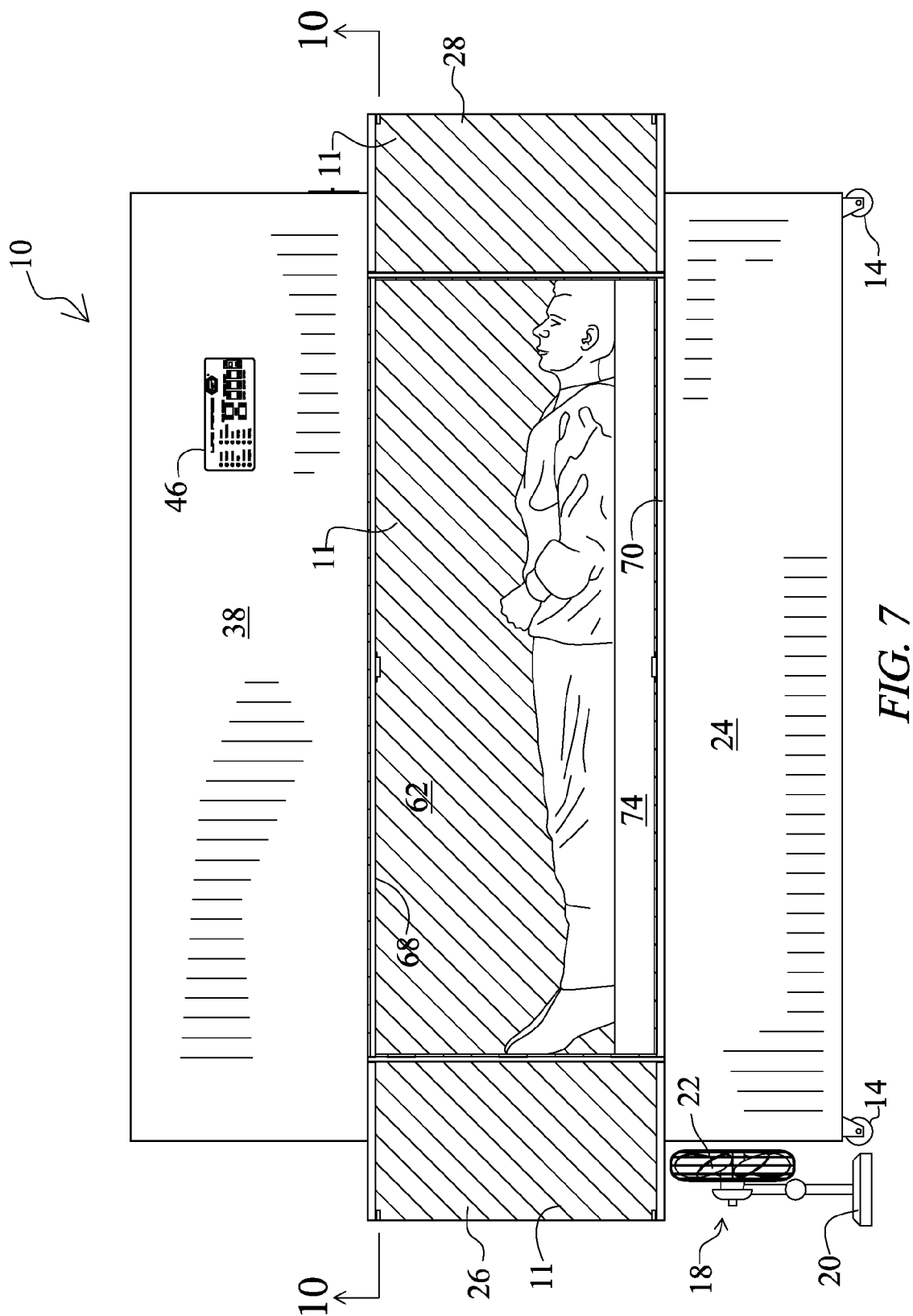
FIG. 7 is a side elevational view of the cabinet when the relaxation chamber is occupied by a user.

FIG. 7 depicts a user lying atop said pad in a supine position.

Figure 8:
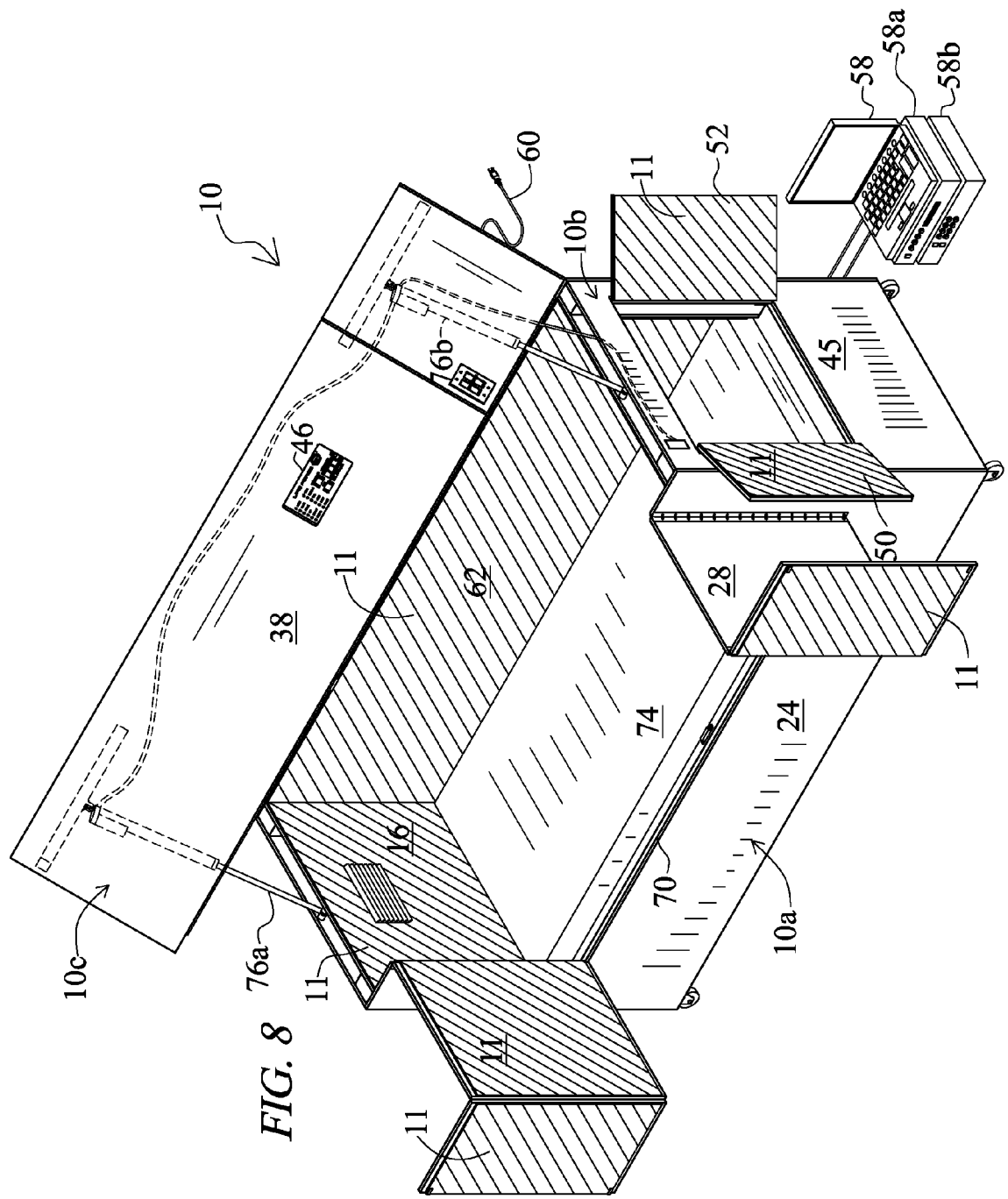
FIG. 8 is a top perspective view when the cabinet lid is in its raised configuration.
Figure 9:
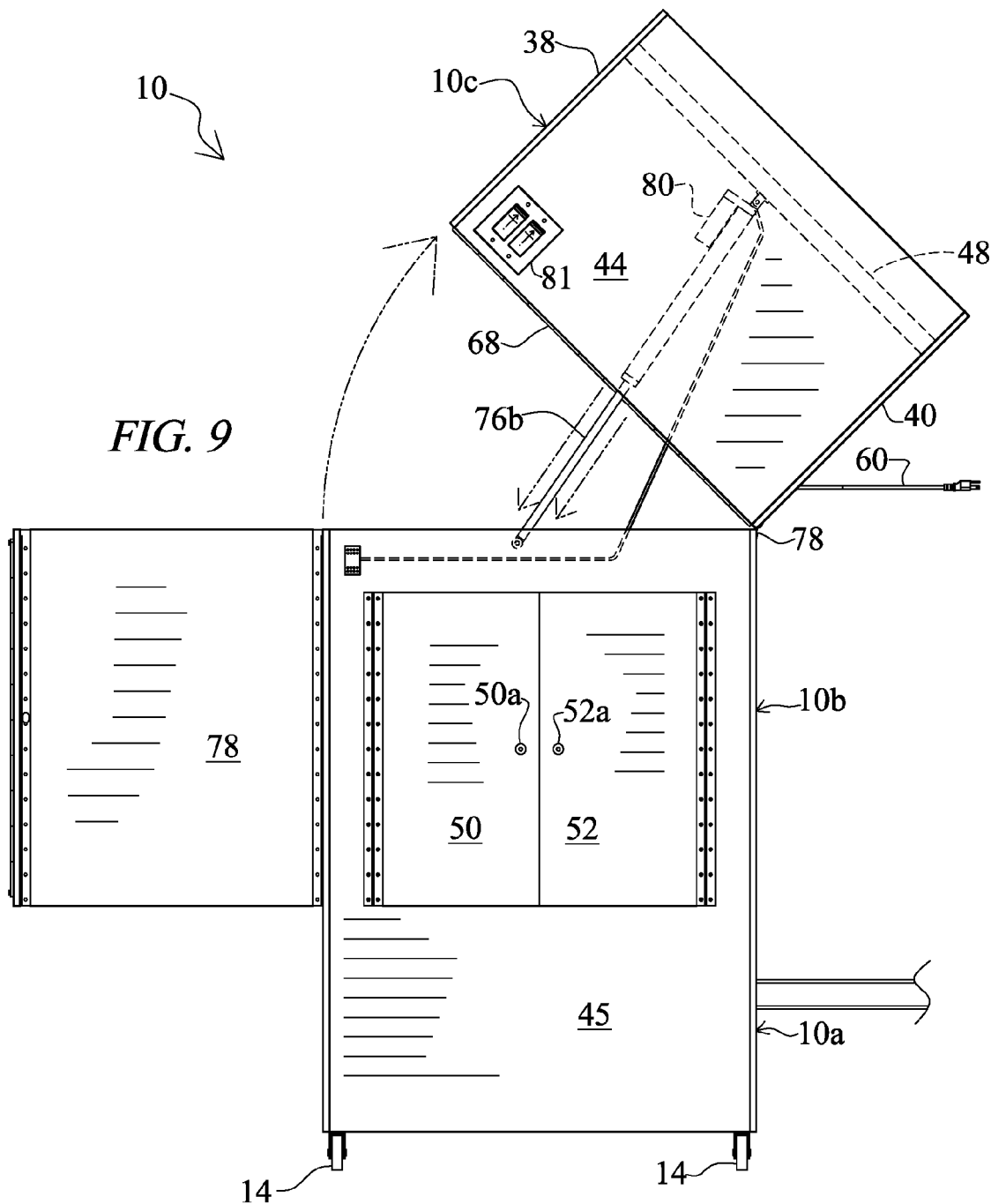
FIG. 9 is a end view when the cabinet lid is in its raised configuration.
Figure 10:
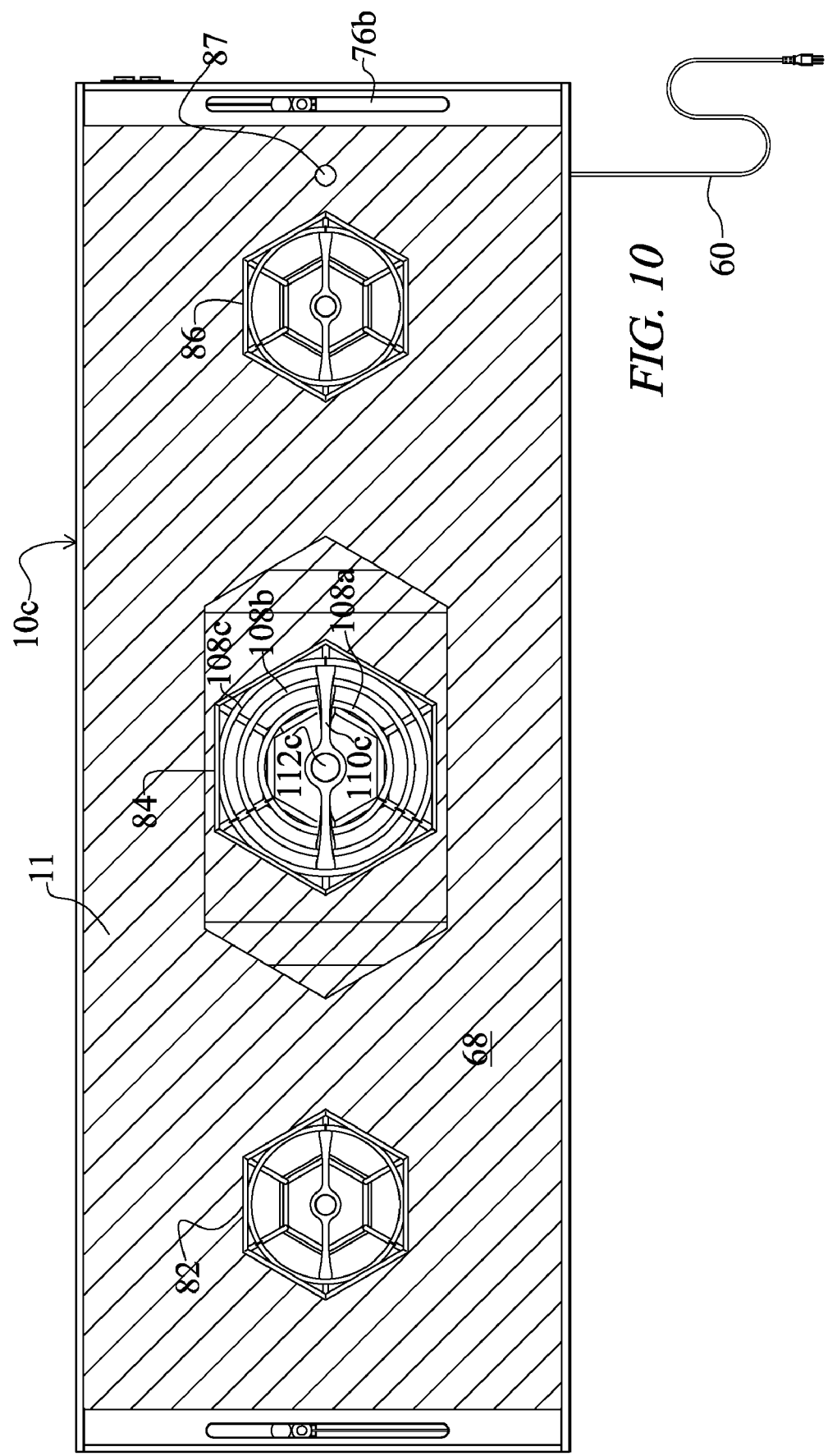
FIG. 10 is a sectional view taken along line 10-10 in FIG. 7.

Upper section 10c is hingedly mounted to middle section 10b. FIGS. 8 and 9 depict telescoping arms 76a, 76b that allow upper section 10c to overlie middle section 10b when said arms are fully retracted and that cause upper section 10c to rotate about hinge 78 into an open position as depicted in said FIGS. 8 and 9 when said arms are in their respective extended positions. The arms are preferably powered by hydraulic motor 80 (FIG. 9). Item 81 is a dimmer switch for dimming the foot and head lights. Fixed position foot light fixture 82, movable middle light fixture 84, and fixed position head light fixture 86 are depicted in FIG. 10. Foot light fixture 82 is so called because it is positioned over the feet of a user. Movable middle light fixture 84 is so called because it is positioned over the middle part of the user's body, and head light fixture 86 is so called because it is positioned over the head of a user when novel apparatus 10 is in use. Item 87 is a camera that records the facial expressions of the client for future analysis.

Light fixture 82 includes light bulb 82a and light fixture 86 includes light bulb 86a. Said light bulbs 82a and 86a are painted with the colors of the rainbow as indicated by the horizontal lines drawn thereon. More particularly, light bulbs 82a and 86a are sold under the trademark The Amazing Rainbow Light® lightbulbs, manufactured by Special FX Lighting, of Hurricane, Utah, on the Internet at fxlight.com/rainbow. No light bulbs are housed within movable middle light fixture 84.

Figure 11:
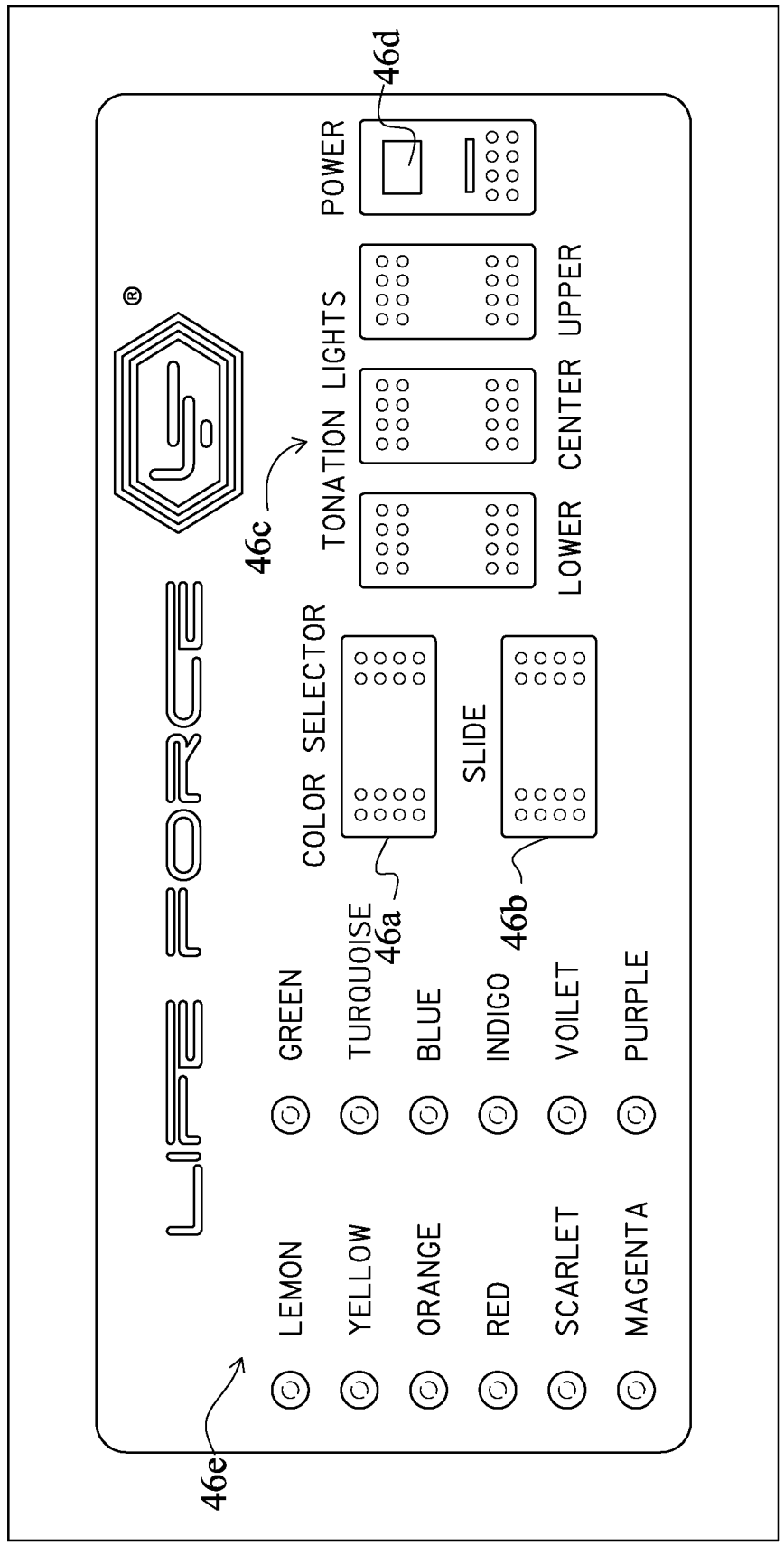
FIG. 11 is a front elevational view of the novel control panel.

Control panel 46 is depicted in detail in FIG. 11. Color selector button 46a performs the function its name expresses. Slide button 46b controls movement of the middle light fixture and the buttons collectively denoted 46c and marked Tonation Lights control illumination in any combination of an array of three light bulbs associated with movable middle light fixture 84. Power switch 46d performs the function its name expresses. In this embodiment, twelve (12) colors are listed and panel lights collectively denoted 46e are illuminated one at a time as the novel device operates in the manner disclosed below.

Figure 12:
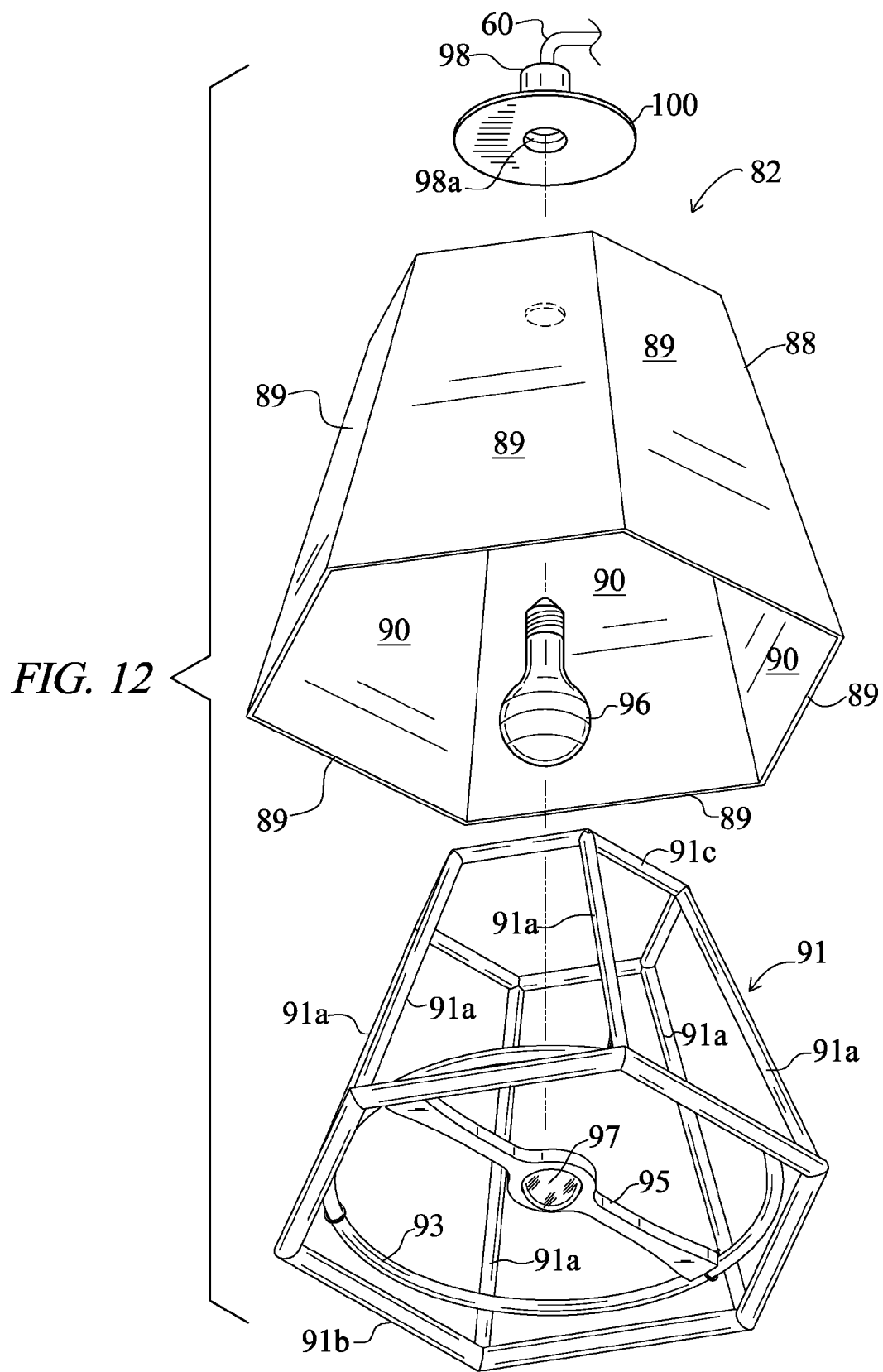
FIG. 12 is an exploded bottom perspective view of a head or foot light fixture.

The foot light and the head light share a common structure. As depicted in the top and bottom perspective views of FIGS. 12 and 13, respectively, hexagonal housing 88 is formed from six (6) panels 89 of quadrilateral shape, each of which is wider at its bottom than its top as depicted. Each hexagonal panel 89 is mirrored as at 90 on its interior surface. Hexagonal panel 92 (FIG. 13) closes the top of the light structure and is centrally apertured as at 94. The base of light bulb 96 extends through said aperture and engages internal threads 98a formed in boss 98 of disc 100. Light bulb 96 is an Amazing Rainbow Light identified above. Each light fixture sits atop wall 68 in registration with hexagonal opening 64 formed in said wall, it being understood that each light fixture is slightly larger than its associated hexagonal opening.

Quadrilateral panels 89 are mounted on hexagonal frame 91 that includes six (6) straight frame members 91a that are equidistantly spaced from one another and secured at their respective lower ends to horizontal hexagonal frame 91b at each angle formed in said frame 91b and at their respective upper ends to horizontal hexagonal frame 91c at each angle formed in said frame 91c. Lower frame 91b is larger in breadth than upper frame 91c. Horizontal ring 93 is mounted within said frame near the lower end thereof. Crystal holder 95 has opposite ends secured to ring 93 and said crystal holder is coincident with a diameter of said ring. Crystal 97 is mounted in the center of crystal holder 95 and crystal holder 95 is made of spruce pine.

Figure 14A:
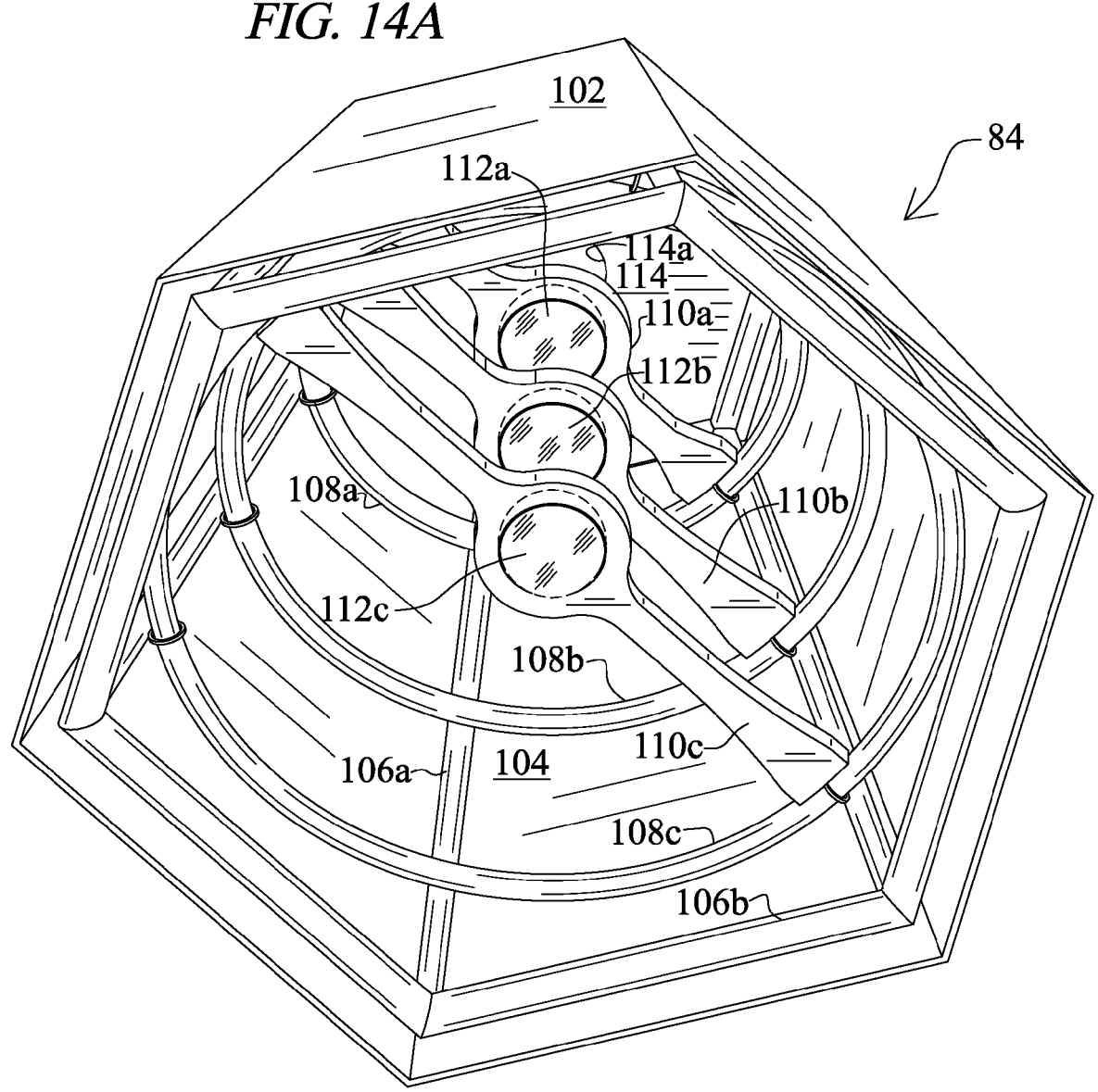
FIG. 14A is a first bottom perspective view of the movable middle light fixture.
Figure 14B:
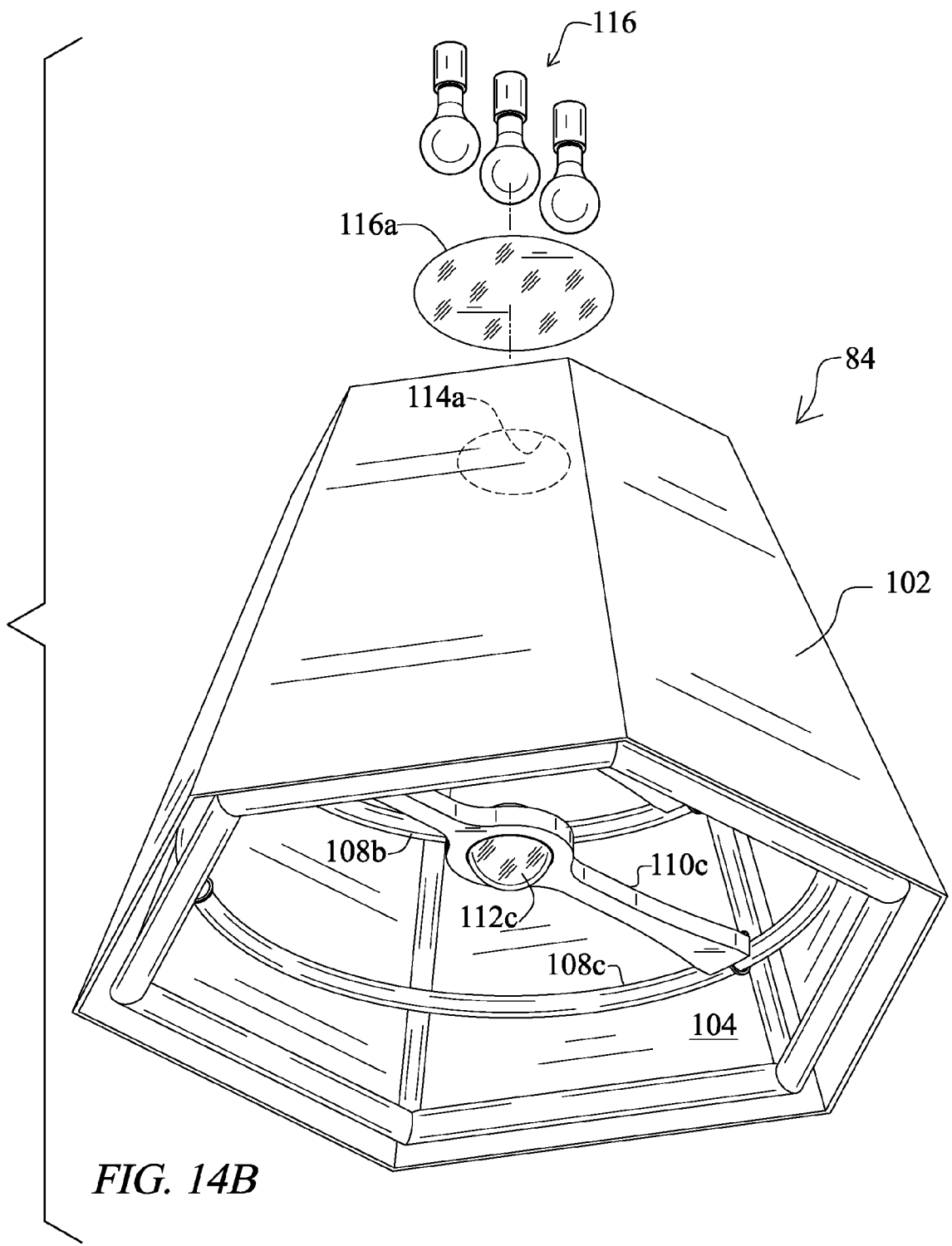
FIG. 14B is a second bottom perspective exploded view of said movable middle light fixture.

Movable middle light fixture 84 is best depicted in FIGS. 14A, 14B, and 14C. Like the foot and head lights, it has a hexagonal structure formed by six quadrilateral panels 102 that are wider at their respective lowers ends than at their respective upper ends. Also like the foot and head lights, the inner surface of each panel is mirrored as ay 104. As best understood in connection with FIG. 14C, quadrilateral panels 102 are mounted on hexagonal frame 106 that includes six (6) straight frame members 106a that are equidistantly spaced from one another and secured at their respective lower ends to horizontal hexagonal frame 106b at each angle formed in said frame 106b and at their respective upper ends to horizontal hexagonal frame 106c at each angle formed in said frame 106c. Lower frame 106b is larger in breadth than upper frame 106c. Three horizontal rings 108a, 108b, and 108c are mounted within said frame in equidistantly and vertically spaced relation to one another, with uppermost ring 108a having a diameter less than middle ring 108b and said middle ring having a diameter less than lower ring 108c. Upper crystal holder 110a has opposite ends secured to upper ring 108a and said upper crystal holder is coincident with a diameter of said upper ring. Middle crystal holder 110b has opposite ends secured to middle ring 108b and said middle crystal holder is coincident with a diameter of said middle ring. Lower crystal holder 110c has opposite ends secured to lower ring 108c and said crystal holder is coincident with a diameter of said lower ring. All three crystal holders share a common orientation when mounted in movable light fixture 84 as best depicted in FIG. 14A.

An aperture is formed mid-length of upper crystal holder 110a and crystal 112a is secured within said aperture. An aperture is also formed mid-length of middle crystal holder 110b and crystal 112b is secured within said aperture. Similarly, an aperture is formed mid-length of lower crystal holder 110c and crystal 112c is secured within said aperture. Each crystal amplifies the effects of the colors of the light that travels through it.

Like the foot and head light fixtures, movable middle light fixture 84 has a hexagonal top wall 114 (FIG. 14A) that is centrally apertured as at 114a as depicted in FIGS. 14A-C. In this embodiment, three (3) light bulbs in linear array, collectively denoted 116, are mounted above hexagonal top wall 114 with the center bulb being centered with respect to aperture 114a. Color disc 118, disclosed in greater detail below, is positioned between light bulbs 116 and central aperture 114a. Light bulbs 116 move conjointly with middle light fixture 84 when said fixture 84 is reciprocated in a manner disclosed hereinafter. The middle light bulb of said three bulb array 116 remains in axial alignment with the vertical axis of symmetry of middle light fixture 84 at all times. Each light bulb 116 is screwed into a conventional base. The bases for said three lights and the bracket in which said bases are mounted is denoted 116b in FIGS. 15A and 15B. The top wall of bracket 116b is secured to horizontal panel 48 that extends between front wall 38 and back wall 40 of upper section 10c of cabinet 10.

FIGS. 15A and 15B depict color disc 118 in more detail. It has a plurality of apertures, collectively denoted 120, formed therein so that said apertures are near the periphery of said disc 118. A colored translucent disc 120a is mounted within each aperture 120 as suggested in the exploded view of FIG. 15A and as depicted in FIG. 15B.

Color disc 118 is also centrally apertured and shaft 122 extends through said central aperture. Shaft 122 is held in place by a first nut 122a that overlies color disc 118 and a second nut 122b that that underlies said disc. Color disc 118 is rotated about shaft 122 by drive disc 124 that abuttingly engages color disc 118 at its periphery. Drive disc 124 is secured to the output shaft of motor 126 and rotates conjointly therewith. Motor 126 is mounted to a first leaf of hinge 126a and a second leaf of said hinge is secured to vertical front panel 39 of the reciprocating housing for movable middle light fixture 84.

As motor 126 operates, drive disc 124 causes rotation of color disc 118. Colored translucent discs 120a therefore pass under light bulb array 116 in sequence when said motor is operating. However, as mentioned above, after a particular colored translucent disc has been selected for its relationship to the sound to be emitted by the speakers, color disc 118 does not rotate.

LED switch disc 128 is centrally apertured and said central aperture receives shaft 122 as indicated in FIGS. 15A and 15B. LED switch disc 128 is positioned in vertically spaced relation above color disc 118 and is concentric therewith. The diameter of LED switch disc 128 is less than that of color disc 118. An imaginary circle drawn on color disc 118 to interconnect the radially innermost point of each aperture 120 would have a diameter slightly larger than a diameter of said LED switch disc. LED switch disc 128 is secured to the underside of horizontal panel 48 by an assembly that includes disc 130 which is disposed below said horizontal panel 48, disc 132 which is disposed above said panel 48 and disc 134 which overlies disc 132. Nut 134*a* engages the uppermost end of shaft 122 to hold said shaft in its upright configuration.

Figure 16:
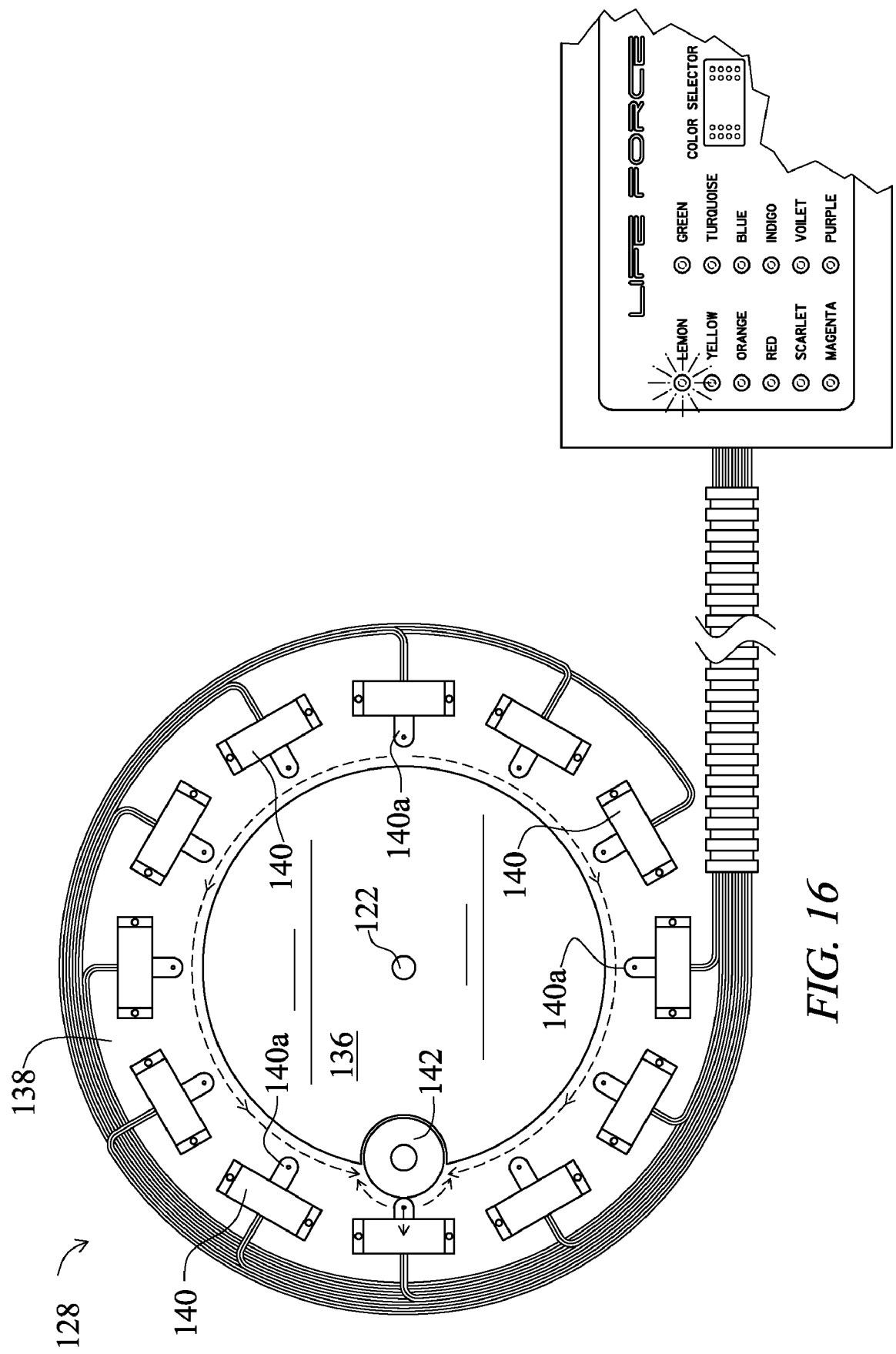
FIG. 16 is a top plan view of an LED disc assembly.

As best depicted in FIG. 16, LED switch disc 128 includes inner disc 136 that rotates conjointly with shaft 122 and outer toroidal plate 138 that is stationary. A plurality of LED switches 140 is mounted about the periphery of toroidal plate 138.

Protrusion 142 is mounted in a recess formed in disc 136 and rotates conjointly with said disc. Each LED switch 140 has a spring-loaded switch actuator 140*a* that is actuated when protrusion 142 abuttingly engages it as depicted at the 9:00 o'clock position of FIG. 16. LED switches 140 are thus sequentially activated, one at a time, as disc 136 rotates about shaft 122, there being one momentary activation of each LED 140 switch and corresponding LEDs 46*e* on control panel 46 for each revolution of disc 136. Each LED on control panel 46 emits a unique color of light relative to the other LEDs.

Figure 17B:
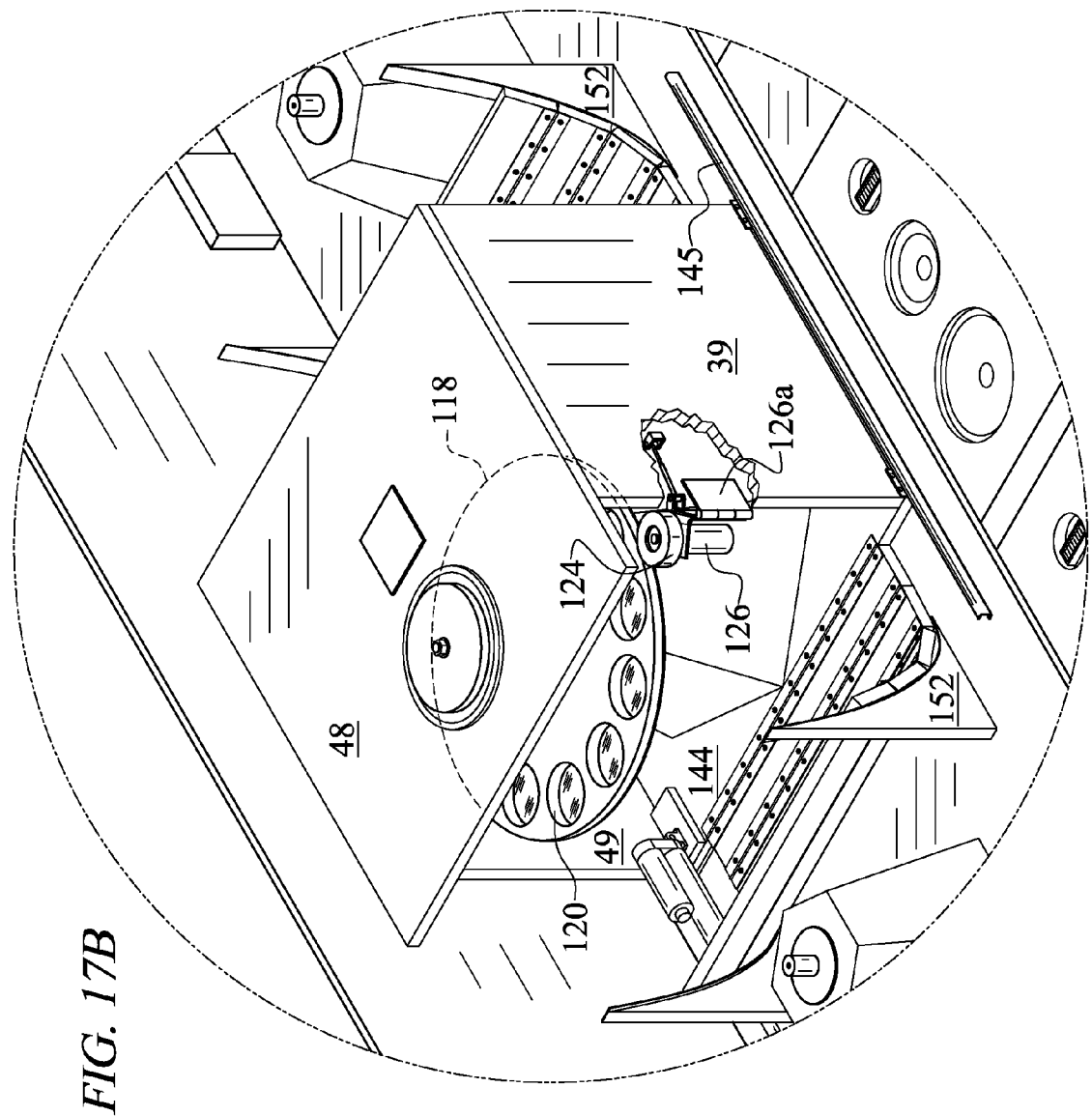
FIG. 17B is an enlarged detailed view of the parts at the top center of FIG. 17A.

FIGS. 17, 18A and 18B depict the mechanism that enables middle light fixture 84 to reciprocate along a longitudinal axis of cabinet 10. Middle light fixture 84 is secured at its widest end to movably mounted flat panel 144 having a hexagonal opening formed centrally thereof. A first transversely disposed rigid strip 146 is hingedly connected by first hinge 148 to a first transversely disposed edge of flat panel 144 and a second transversely disposed rigid strip, also denoted 146, is hingedly connected by a second hinge, also denoted 148, to a second transversely disposed edge of said flat panel 144 as depicted in FIG. 17. Additional rigid strips 146 of the same structure are connected to one another in the same way by similar hinges to form first and second flexible panels, collectively denoted 150.

FIGS. 18A and 18B also depict Estonian tone-wood slats 11 oriented at a forty five degree (45°) angle relative to the respective surfaces that they cover. Slats 11 direct sound in a circular fashion as indicated by the arrows included in said Figs.

The respective opposite ends of the first and second panels are supported by ramps, collectively denoted 152. Accordingly, when middle light fixture 84 moves from the foot end of cabinet 10 to the head end thereof, the flexible panel on the foot end of cabinet 10 slides down its ramp and the flexible panel on the head end of said cabinet slides up its ramp. When middle light fixture 84 moves from the head end of cabinet 10 to the foot end thereof, the flexible panel on the head end of cabinet 10 slides down its ramp and the flexible panel on the foot end of said cabinet slides up its ramp.

Each flexible wing is formed by hingedly connecting contiguous panels of a plurality of rigid panels to one another as illustrated and as disclosed above, although such wings could be provided in many different ways. For example, each wing could be supplanted by a flexible sheet of material so that no hinges would be required. However, such material might warp over time so the preferred wings are formed by said plurality of interconnected rigid panels.

Reciprocal motion of flat panel 144 is effectuated by hydraulic linear actuator 154. Said arm 154 has a first stationary end 156 mounted to top wall 68 and a second end mounted to block 158 that is secured to flat panel 144. Flat panel 144 is slideably mounted for longitudinal reciprocation as hydraulic arm 154 is extended and retracted as indicated by doubleheaded directional arrow 160. Flat panel 144 is connected at its leading and trailing edges to horizontal panel 48 by vertical front panel 39 and vertical back panel 49. Flat panel 144 slides on bearings, not depicted, mounted in linear track 145 depicted in 17B).

FIG. 18A depicts flat panel 144, flexible panels 150, and cabinet 10 in bottom perspective and FIG. 18B provides a top perspective view thereof.

Figure 19A:
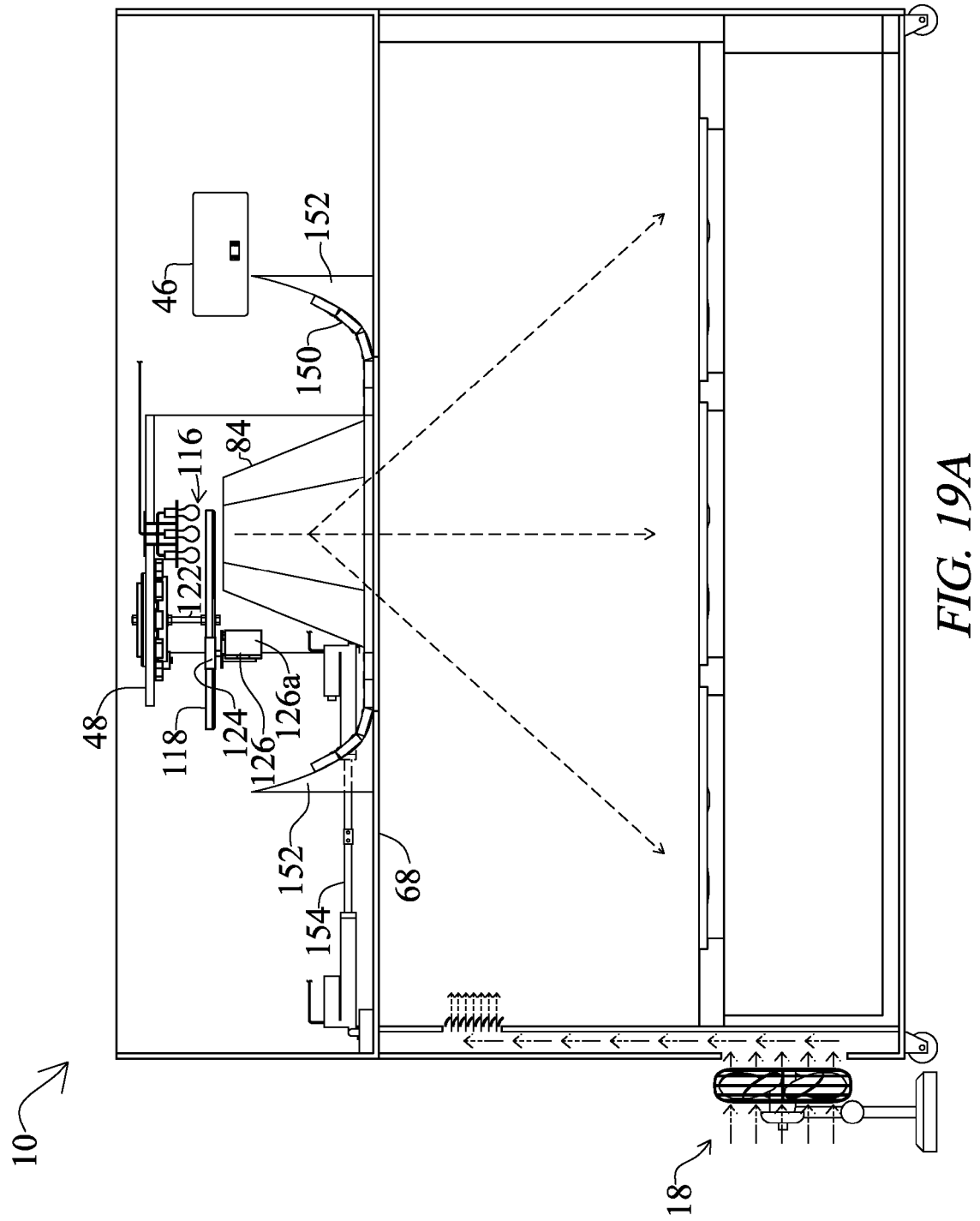
FIG. 19A is a sectional view taken along line 19A-19A in FIG. 2.
Figure 19B:
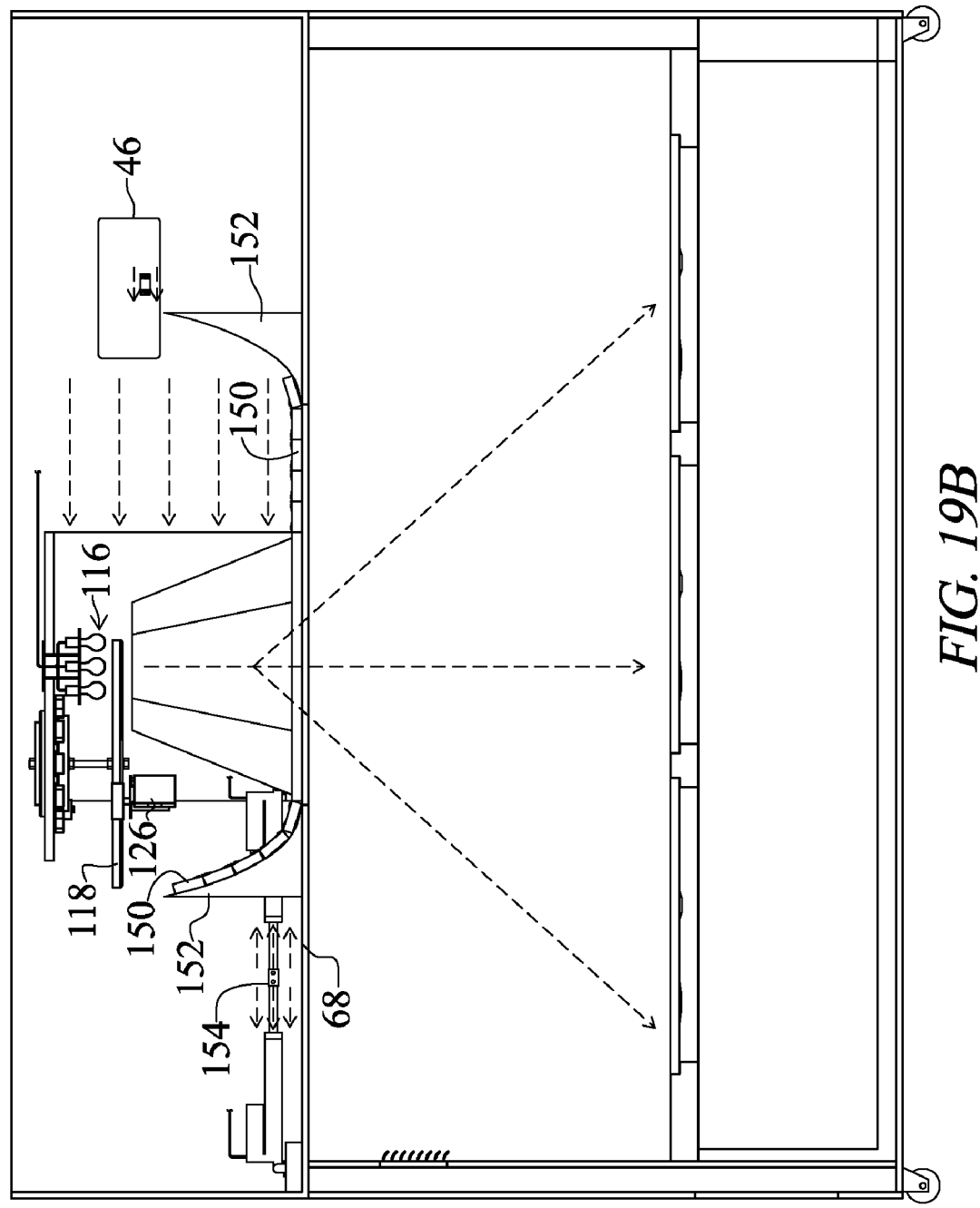
FIG. 19B is a sectional view like that of FIG. 19A but with the middle light fixture in its foot position.

As best depicted in FIGS. 19A-G, LED switch disc 128 is mounted in underlying relation to flat panel 48 in vertically spaced relation to color disc 118 having translucent discs 120*a* mounted about its periphery. LED switch disc 128 is mounted above movable middle light fixture 84 in offset relation thereto. Color disc 118 is rotated to bring translucent colored discs 120*a* into centered relation to central aperture 114*a* (FIG. 14B) formed in the hexagonal top panel of middle light fixture 84. As depicted in FIG. 19B, this aligns the middle light bulb of light bulb array 116 with said central aperture 114*a*. Accordingly, the longitudinal axis of symmetry of said middle light bulb is coincident with the longitudinal axis of symmetry of movable middle light fixture 84.

When cabinet 10 is configured as depicted in FIG. 19A, movable middle light fixture 84 is centered, mid-length of said cabinet. Only the center light bulb of light bulb array 116 is illuminated and the light therefrom is diffused so it is reflected from the mirrored surfaces of said fixture 84 but the axis of symmetry of the diffused light is centered within cabinet 10 as indicated by the dotted directional arrow. FIG. 19B depicts the same illumination when movable middle light fixture 84 is moved to its maximum extent in the direction of the foot end of the cabinet and FIG. 19C depicts the same illumination when movable middle light fixture 84 is moved to its maximum extent in the direction of the head end of the cabinet.

Figure 19C:
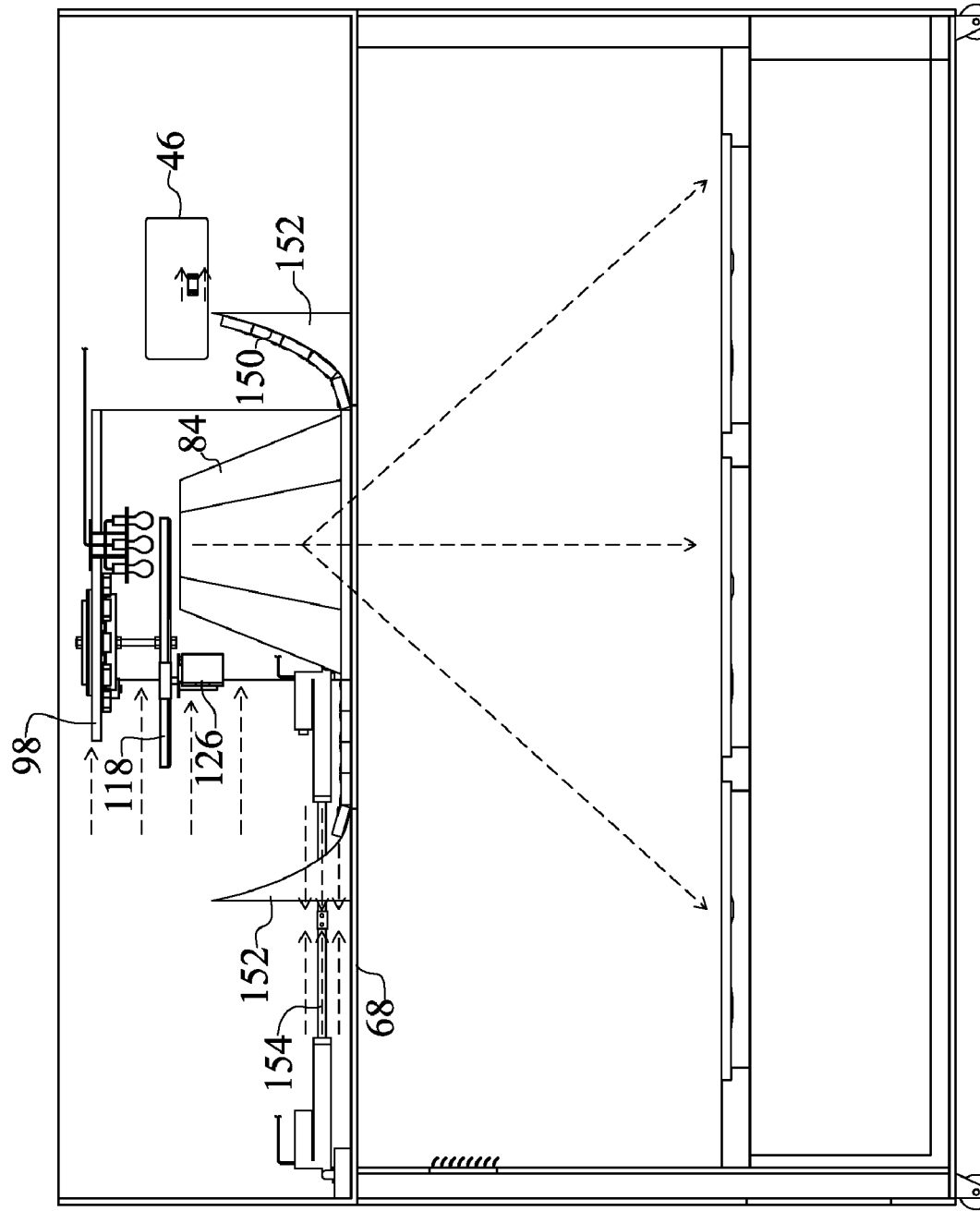
FIG. 19C is a sectional view like that of FIG. 19A but with the middle light fixture in its head position.
Figure 19D:
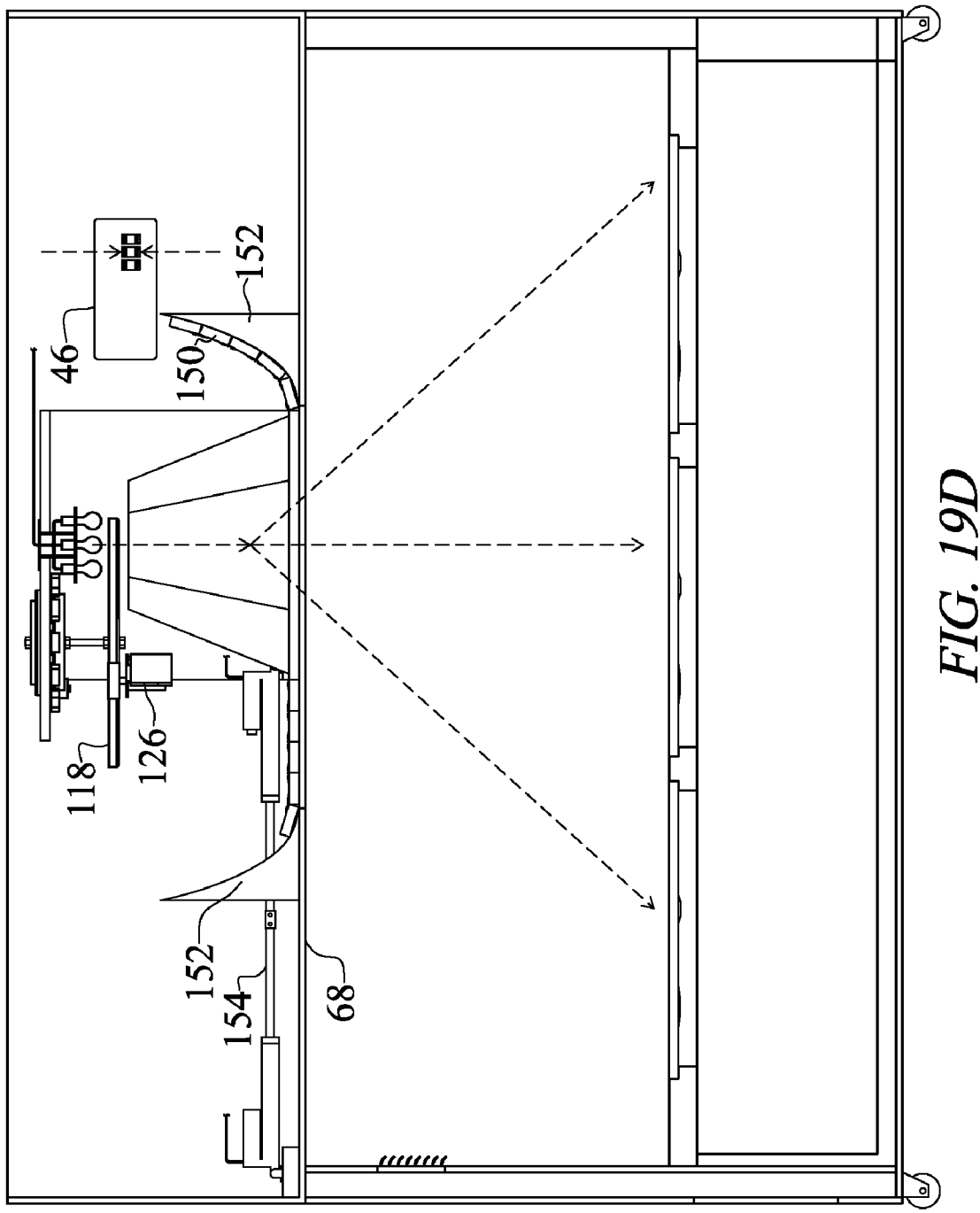
FIG. 19D is a sectional view like that of FIG. 19C, depicting the middle light of a three light bulb array in its illuminated state.

FIG. 19D is the same as FIG. 19C but the two additional elongated, diverging dotted arrows indicate the respective foot and head ends of the diffused light beam from said center light bulb. Another pair of truncate, vertical arrows that are directed toward one another on control panel 46 indicates that the center light bulb of light bulb array 116 is illuminated.

Figure 19E:
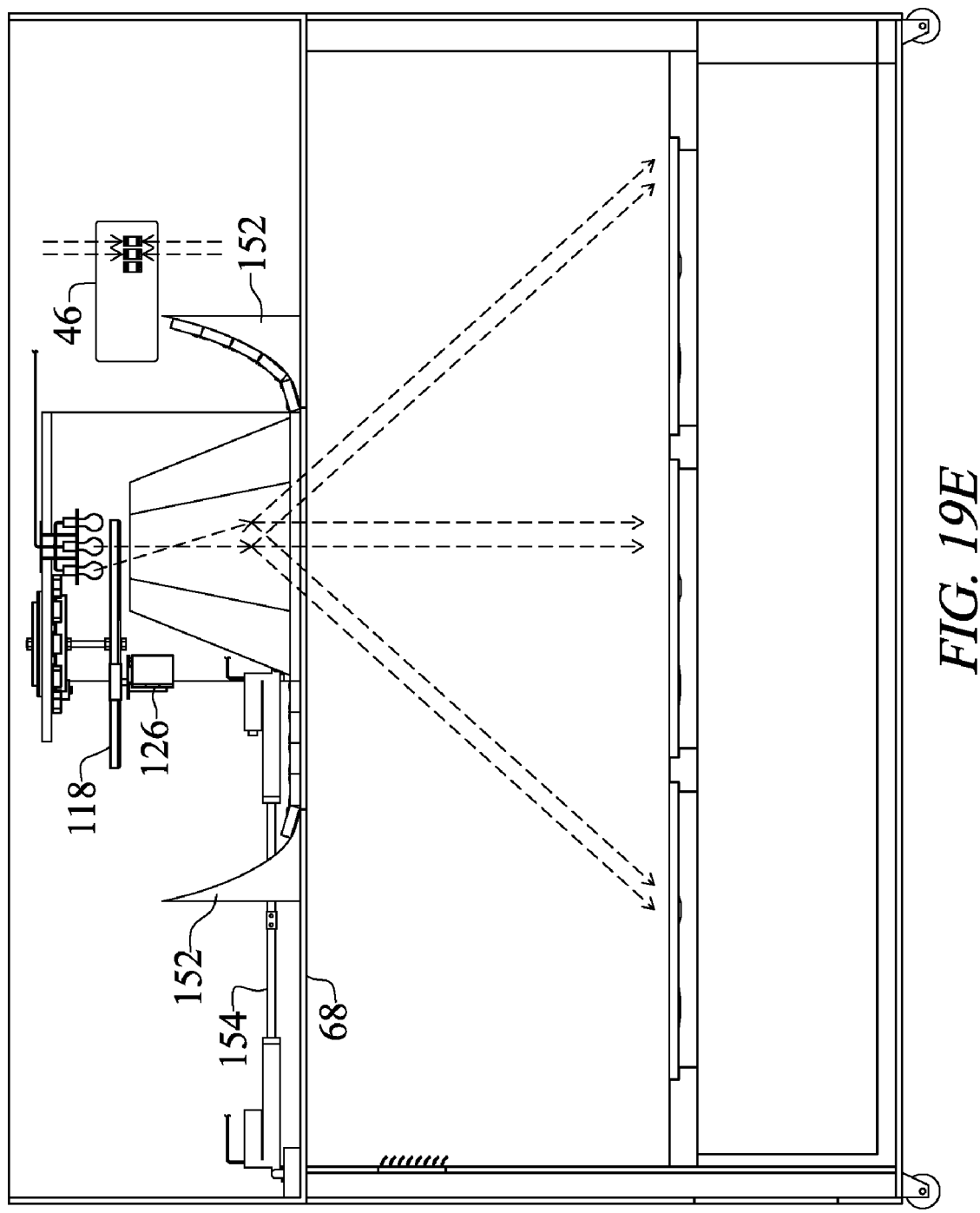
FIG. 19E is a sectional view like that of FIG. 19C, depicting the middle light and a first end light of a three light bulb array in their respective illuminated states.

FIG. 19E is also like FIG. 19D except that the rightmost light bulb of light bulb array 116 is illuminated as indicated by the truncate arrows on control panel 46, thereby producing a different lighting effect as indicated by the elongate dotted arrows.

Figure 19F:
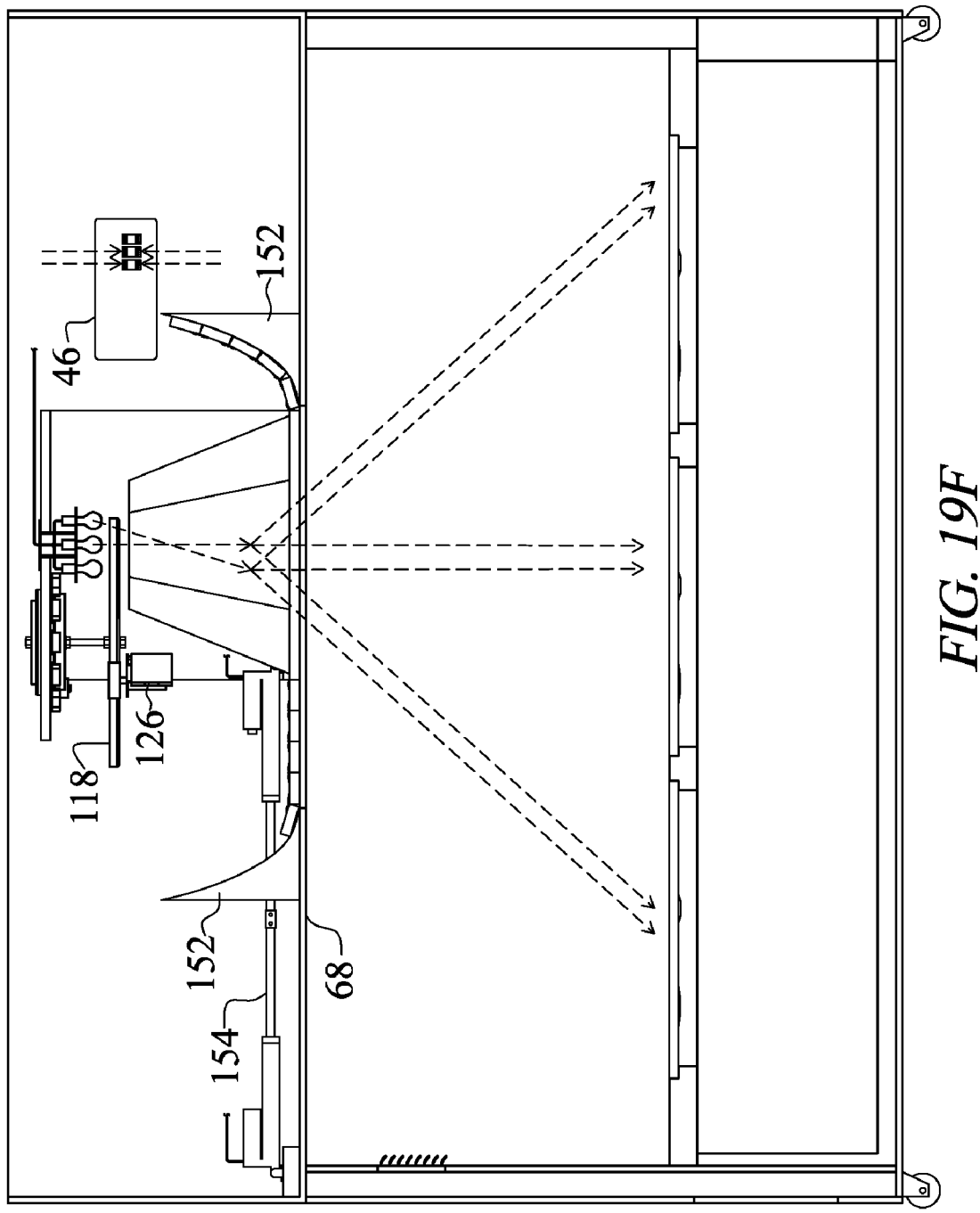
FIG. 19F is a sectional view like that of FIG. 19C, depicting the middle light and a second end light of said three light bulb array in their respective illuminated states.

FIG. 19F is also like FIG. 19D except that the leftmost light bulb of light bulb array 116 and the center light bulb are illuminated as indicated by the truncate arrows on control panel 46, thereby producing a different lighting effect as indicated by the elongate dotted arrows.

Figure 19G:
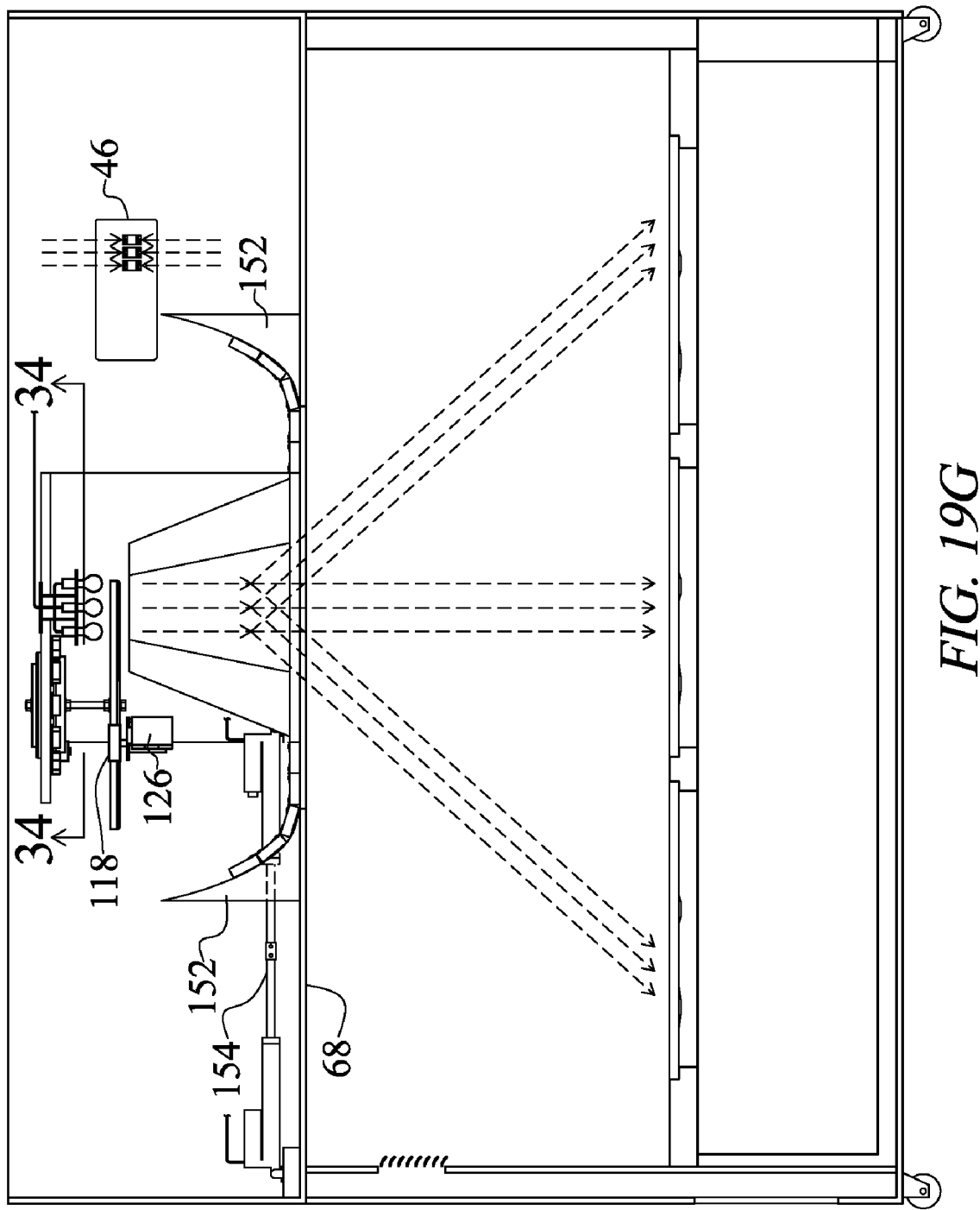
FIG. 19G is a sectional view like that of FIG. 19C, all three of said three light bulbs in said light bulb array in their respective illuminated states and said movable middle light fixture in its centered position.

FIG. 19G is also like FIG. 19D except that all three of the light bulbs of light bulb array 116 are illuminated as indicated by the truncate arrows on control panel 46, thereby producing a different lighting effect as indicated by the elongate dotted arrows.

Figure 20:
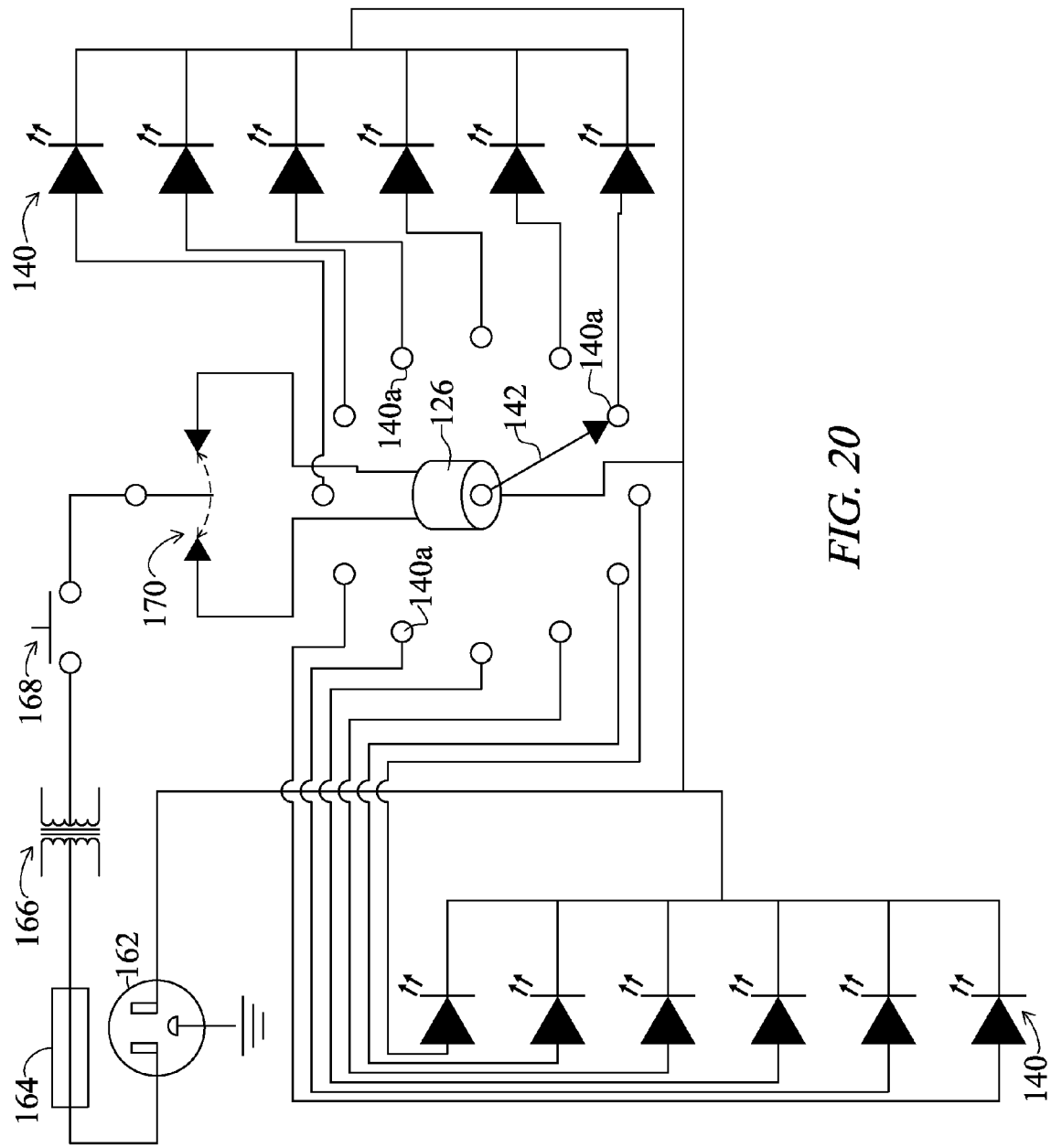
FIG. 20 is a diagram of the electrical circuitry that sequentially illuminates the LEDs of this invention.

FIG. 20 is a diagram of the electrical circuitry that operates LEDs 140. Power source 162 is in series electrical communication with fuse 164, transformer 166, switch 168, bidirectional switch 170, and motor 126. As disclosed above, motor 126 rotates shaft 122 that causes rotation of color disc 118 and disc 136 (FIG. 16) that carries protuberance 142 to sequentially illuminate LEDs 140.

FIG. 21 depicts cabinet 10 in use with all three of the light bulbs in light bulb array illuminated, with the foot and head lamps illuminated, with movable middle light fixture 84 in its centered position mid-length of cabinet 10.

It will thus be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense. The following claims are intended to cover all of the generic and specific features of the invention herein disclosed, and all statements of the scope of the invention that, as a matter of language, might be said to fall therebetween.

What is claimed is:

1. A cabinet that includes a relaxation chamber, comprising:
   said cabinet including a base section, a middle section, and an upper section;
   said base section adapted to enclose a plurality of speakers;
   said middle section including said relaxation chamber and being adapted to enclose a human user of said relaxation chamber when said human user is in a reclining position;
   said middle section having a foot end, a middle section, and a head end corresponding to the feet, torso and head of said user;
   said upper section adapted to house a plurality of light fixtures;
   said light fixtures including light bulbs that emit light at preselected frequencies;
   said speakers adapted to emit sound in harmonic relation to said preselected frequencies;
   said middle section including a bottom wall;
   a plurality of openings formed in said bottom wall;
   a speaker housing disposed in closing relation to each opening of said plurality of openings;
   a plurality of openings formed in each of said speaker housings;
   a speaker disposed in sound-emitting registration with each of said speaker housing openings;
   a first plurality of speakers positioned on opposite sides of a longitudinal axis of symmetry of said bottom wall of said middle section in longitudinally spaced relation to one another; and
   a second plurality of speakers positioned in coincidence with said longitudinal axis of symmetry of said bottom wall in longitudinally spaced relation to one another.

2. The cabinet of claim 1, further comprising:
   a stationary foot light fixture including a light bulb disposed in said upper section in illuminating relation to said middle section, said foot light fixture being disposed at said foot end of said relaxation chamber.

3. The cabinet of claim 2, further comprising:
   a stationary head light fixture including a light bulb disposed in said upper section in illuminating relation to said middle section, said head light fixture being disposed at said head end of said relaxation chamber.

4. The cabinet of claim 3, further comprising:
   a movably mounted middle light fixture disposed in said upper section in illuminating relation to said middle section, said movably mounted middle light fixture being disposed above said middle section of said cabinet.

5. The cabinet of claim 4, further comprising:
   said foot light fixture having a hexagonal housing formed from six panels of quadrilateral shape, each of which is wider at its bottom than its top;
   each of said quadrilateral panels being mirrored on an interior surface thereof;
   a hexagonal panel disposed in closing relation to a top of said foot light fixture;
   a central aperture formed in said hexagonal panel, said central aperture adapted to accommodate a base of a light bulb extending through said aperture;
   a socket for electrically engaging said base of said light bulb being mounted atop said hexagonal panel is registration with said central opening.

6. The cabinet of claim 4, further comprising:
   said head light fixture having a hexagonal housing formed from six panels of quadrilateral shape, each of which is wider at its bottom than its top;
   each of said quadrilateral panels being mirrored on an interior surface thereof;
   a hexagonal panel disposed in closing relation to a top of said head light fixture;
   a central aperture formed in said hexagonal panel, said central aperture adapted to accommodate a base of a light bulb extending through said aperture;
   a socket for electrically engaging said base of said light bulb being mounted atop said hexagonal panel is registration with said central opening.

7. The cabinet of claim 4, further comprising:
   said upper section including a front wall, a back wall, a first end wall, a second end wall and a bottom wall that is a top wall of said middle section;
   a movable housing that houses said movable middle light fixture, said movable housing including a top horizontal panel, a bottom horizontal panel, a front vertical panel and a back vertical panel that interconnect said top and bottom horizontal panels to one another along front and back edges thereof, respectively, said movable housing being positioned in said upper section;
   said movable middle light fixture being mounted to said movable housing for conjoint movement therewith;
   said movable middle light fixture having a hexagonal structure formed by six quadrilateral panels that are wider at their respective lowers ends than at their respective upper ends;
   each of said quadrilateral panels having a mirrored inner surface;
   said quadrilateral panels of said movable middle light fixture being mounted on a hexagonal frame.

8. The cabinet of claim 7, further comprising:
   said hexagonal frame being made of copper.

9. The cabinet of claim 7, further comprising:
   a plurality of horizontal rings being mounted within said hexagonal frame in equidistantly and vertically spaced relation to one another, an uppermost ring having a diameter less than a middle ring and said middle ring having a diameter less than a lower ring.

10. The cabinet of claim 9, further comprising:
    an upper crystal holder having opposite ends secured to said upper ring and said upper crystal holder being coincident with a diameter of said upper ring;
    a middle crystal holder having opposite ends secured to said middle ring and said middle crystal holder being coincident with a diameter of said middle ring;
    a lower crystal holder having opposite ends secured to said lower ring and said lower crystal holder being coincident with a diameter of said lower ring;
    a first aperture formed mid-length of said upper crystal holder and a first crystal secured within said first aperture;
    a second aperture formed mid-length of said middle crystal holder and a second crystal secured within said second aperture;

a third aperture formed mid-length of said lower crystal holder and a third crystal secured within said third aperture.

11. The cabinet of claim 7, further comprising:
said movable middle light fixture having a hexagonal top wall that is centrally apertured;
a plurality of light bulbs in linear array disposed above said hexagonal top wall, a center bulb of said plurality of light bulbs in linear array being centered with respect to said central aperture;
a colored, translucent disc positioned between said plurality of light bulbs in linear array and said central aperture;
said plurality of light bulbs in linear array being mounted to said movable housing so that said plurality of light bulbs in linear array moves conjointly with said movable middle light fixture when said movable middle light fixture is reciprocated; and
a middle light bulb of said plurality of light bulbs in linear array remaining in axial alignment with the vertical axis of symmetry of said movable middle light fixture when said movable middle light fixture reciprocates.

12. The cabinet of claim 11, further comprising:
a color disc having a plurality of apertures formed therein near the periphery of said color disc;
a translucent colored disc being mounted within each aperture of said plurality of apertures, each translucent colored disc having a color unique to it;
a central aperture formed in said color disc;
a shaft extending through said central aperture;
a drive disc disposed in abutting relation to a peripheral edge of said color disc so that rotation of said drive disc effects rotation of said color disc about said shaft; and
a motor having an output shaft to which said drive disc is secured so that operation of said motor effects rotation of said color disc so that said translucent colored discs sequentially follow a path of travel under said light bulb array.

13. The cabinet of claim 12, further comprising:
an LED switch disc that includes a rotatably-mounted disc-shaped central part and a stationary toroidal part that surrounds said central part in coplanar relation therewith;
a central aperture formed in said central part, said central aperture receiving said shaft and said central part rotating conjointly with said shaft when said shaft rotates;
said LED switch disc being positioned within said movable housing in vertically spaced relation above said color disc and being concentric therewith;
said LED switch disc having a diameter less than a diameter of said color disc; and
a plurality of LED switches mounted about the periphery of said toroidal part.

14. The cabinet of claim 13, further comprising:
a recess formed in a peripheral edge of said rotatable central part of said LED switch disc;
a protuberance mounted in said recess for conjoint rotation with said rotatable central part;
a spring-loaded switch actuator forming a part of each LED switch;
each switch actuator being actuated when said protuberance abuttingly sequentially engages it as said central part of said LED switch disc rotates about said shaft, there being one momentary activation of each LED switch for each revolution of said central part.

15. The cabinet of claim 14, further comprising:
reciprocating means for reciprocating said movable housing and hence said middle light fixture along a longitudinal axis of said cabinet;
said bottom horizontal panel of said movable housing having a hexagonal opening formed centrally thereof;
a lower end of said movable middle light fixture being disposed in registration with said hexagonal opening;
a first transversely disposed rigid strip hingedly connected by a first hinge to a first transversely disposed edge of said bottom horizontal panel and a second transversely disposed rigid strip hingedly connected by a second hinge to a second transversely disposed edge of said bottom horizontal panel;
a plurality of additional rigid strips having the same structure as said first rigid strip being connected to one another in the same way by similar hinges to form first and second flexible panels;
respective opposite ends of said first and second panels being supported by ramps so that when said movable middle light fixture moves from the foot end of said cabinet to the head end thereof, the flexible panel on the foot end of said bottom horizontal panel slides down its ramp and the flexible panel on the head end of said bottom horizontal panel slides up its ramp and so that when said movable middle light fixture moves from the head end of said cabinet to the foot end thereof, the flexible panel on the head end of said cabinet slides down its ramp and the flexible panel on the foot end of said cabinet slides up its ramp.

16. The cabinet of claim 15, further comprising:
a hydraulic linear actuator for effecting said reciprocal motion of said movable housing;
said hydraulic linear actuator having a first stationary end secured to said bottom wall of said top section and a movable second end secured to said bottom horizontal panel of said movable housing.

17. The cabinet of claim 16, further comprising:
said LED switch disc being mounted in underlying relation to said top horizontal panel in vertically spaced relation to said color disc;
said color disc being mounted above said movable middle light fixture in offset relation thereto so that as said color disc rotates, said translucent colored discs are brought into centered relation to said central aperture formed in said hexagonal top panel of said movable middle light fixture to align a middle light bulb of said light bulb array with said central aperture, said longitudinal axis of symmetry of said middle light bulb being coincident with a longitudinal axis of symmetry of said movable middle light fixture.

18. The cabinet of claim 13, further comprising:
a control panel mounted on said front wall;
said control panel including a color selector button, a slide button that controls movement of the movable middle light fixture, a plurality of buttons that control illumination in any combination of said array of three light bulbs associated with said movable middle light fixture, a power switch, and a plurality of lights that are illuminated one at a time to indicate which LED switch of said plurality of LED switches is activated.

19. The cabinet of claim 13, further comprising:
a computer electrically connected to said speakers, said computer serving as a signal source for said speakers.

20. The cabinet of claim 13, further comprising:
said middle section, including said bottom horizontal panel of said movable housing and said flexible strips, said end walls of said middle section, said front and back walls of said middle section, and respective interior surfaces of said doors hingedly connected to said middle section being covered with wooden slats that are oriented at a forty-five degree (45°) angle relative to surfaces they cover.

21. The cabinet of claim 20, further comprising:
said wooden slats being Estonian tone-wood slats.

22. The cabinet of claim 1, further comprising:
a pad disposed in overlying relation to said speakers to protect the speakers and to provide a comfortable support for said user.

23. The cabinet of claim 1, further comprising:
a circular aperture formed in said first upstanding rectangular end wall of said base section;
a fan disposed in registration with said circular aperture so that said base section is ventilated when said fan is operating.

24. The cabinet of claim 1, further comprising:
a first hinge for hingedly interconnecting a first door to said front wall;
a second hinge for hingedly interconnecting a second door to said front wall; and
a hinge disposed mid-length of said first door and a hinge disposed mid-length of said second door.

25. The cabinet of claim 1, further comprising:
a plurality of cylindrical housings disposed on said longitudinal axis of symmetry of said bottom wall of said middle section in longitudinally spaced relation to one another;
each cylindrical housing of said plurality of cylindrical housings having diametrically opposed apertures formed therein;
each cylindrical housing including an axle having opposite ends disposed in said diametrically opposed apertures for receiving opposite ends of said axle,
a merkaba crystal rotatably mounted on each axle.

26. The cabinet of claim 25, further comprising:
said upper section being hingedly mounted to said middle section;
a pair of telescoping arms that allow said upper section to overlie said middle section when said arms are fully retracted and that cause said upper section to rotate about a hinge into an open position when said arms are in their respective extended positions, said arms being powered by a hydraulic linear actuator.

27. The cabinet of claim 26, further comprising:
said middle section including a bottom wall, first and second upstanding end walls, an upstanding front wall, an upstanding back wall and a top wall, said bottom wall providing a top wall for said base section and said top wall providing a bottom wall for said upper section;
said upstanding front wall having an opening formed therein that is closed by hingedly mounted doors.

28. A cabinet that includes a relaxation chamber, comprising:
said cabinet including a base section, a middle section, and an upper section;
said base section adapted to enclose a plurality of speakers;
said middle section including said relaxation chamber and being adapted to enclose a human user of said relaxation chamber when said human user is in a reclining position;
said middle section having a foot end, a middle section, and a head end corresponding to the feet, torso and head of said user;
said upper section adapted to house a plurality of light fixtures;
said light fixtures including light bulbs that emit light at preselected frequencies;
said speakers adapted to emit sound in harmonic relation to said preselected frequencies;
a stationary foot light fixture including a light bulb disposed in said upper section in illuminating relation to said middle section, said foot light fixture being disposed at said foot end of said relaxation chamber;
a stationary head light fixture including a light bulb disposed in said upper section in illuminating relation to said middle section, said head light fixture being disposed at said head end of said relaxation chamber;
a movably mounted middle light fixture disposed in said upper section in illuminating relation to said middle section, said movably mounted middle light fixture being disposed above said middle section of said cabinet;
said foot light fixture having a hexagonal housing formed from six panels of quadrilateral shape, each of which is wider at its bottom than its top;
each of said quadrilateral panels being mirrored on an interior surface thereof;
a hexagonal panel disposed in closing relation to a top of said foot light fixture;
a central aperture formed in said hexagonal panel, said central aperture adapted to accommodate a base of a light bulb extending through said aperture;
a socket for electrically engaging said base of said light bulb being mounted atop said hexagonal panel in registration with said central aperture;
said head light fixture having a hexagonal housing formed from six panels of quadrilateral shape, each of which is wider at its bottom than its top;
each of said quadrilateral panels being mirrored on an interior surface thereof;
a hexagonal panel disposed in closing relation to a top of said head light fixture;
a central aperture formed in said hexagonal panel, said central aperture adapted to accommodate a base of a light bulb extending through said aperture;
a socket for electrically engaging said base of said light bulb being mounted atop said hexagonal panel in registration with said central opening;
said upper section including a front wall, a back wall, a first end wall, a second end wall and a bottom wall that is a top wall of said middle section;
a movable housing that houses said movable middle light fixture, said movable housing including a top horizontal panel, a bottom horizontal panel, a front vertical panel and a back vertical panel that interconnect said top and bottom horizontal panels to one another along front and back edges thereof, respectively, said movable housing being positioned in said upper section;
said movable middle light fixture being mounted to said movable housing for conjoint movement therewith;
said movable middle light fixture having a hexagonal structure formed by six quadrilateral panels that are wider at their respective lowers ends than at their respective upper ends;
each of said quadrilateral panels having a mirrored inner surface;
said quadrilateral panels of said movable middle light fixture being mounted on a hexagonal frame;
a plurality of horizontal rings being mounted within said hexagonal frame in equidistantly and vertically spaced relation to one another, an uppermost ring having a diameter less than a middle ring and said middle ring having a diameter less than a lower ring;

an upper crystal holder having opposite ends secured to said upper ring and said upper crystal holder being coincident with a diameter of said upper ring;

a middle crystal holder having opposite ends secured to said middle ring and said middle crystal holder being coincident with a diameter of said middle ring;

a lower crystal holder having opposite ends secured to said lower ring and said lower crystal holder being coincident with a diameter of said lower ring;

a first aperture formed mid-length of said upper crystal holder and a first crystal secured within said first aperture;

a second aperture formed mid-length of said middle crystal holder and a second crystal secured within said second aperture; and a third aperture formed mid-length of said lower crystal holder and a third crystal secured within said third aperture.

* * * * *